(12) United States Patent
Ishida et al.

(10) Patent No.: US 9,599,943 B2
(45) Date of Patent: Mar. 21, 2017

(54) IMAGE FORMING APPARATUS AND RECORDING MATERIAL DETERMINATION UNIT

(71) Applicant: CANON KABUSHIKI KAISHA, Tokyo (JP)

(72) Inventors: Tsutomu Ishida, Suntou-gun (JP); Masafumi Monde, Yokohama (JP); Takuya Shono, Suntou-gun (JP); Kohki Abiko, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/941,103

(22) Filed: Nov. 13, 2015

(65) Prior Publication Data

US 2016/0139550 A1    May 19, 2016

(30) Foreign Application Priority Data

Nov. 17, 2014  (JP) ................................ 2014-233131
Nov. 28, 2014  (JP) ................................ 2014-242303

(51) Int. Cl.
*G03G 15/00* (2006.01)
*G01N 29/11* (2006.01)
*G01N 29/06* (2006.01)

(52) U.S. Cl.
CPC ..... *G03G 15/5029* (2013.01); *G01N 29/0654* (2013.01); *G01N 29/11* (2013.01); *G01N 2291/048* (2013.01); *G01N 2291/102* (2013.01); *G03G 2215/00637* (2013.01)

(58) Field of Classification Search
CPC ................................................ G03G 15/5029
See application file for complete search history.

(56) References Cited

U.S. PATENT DOCUMENTS

2009/0003857 A1*  1/2009  Kuramochi .............. B65H 7/02
                                                                      399/45

FOREIGN PATENT DOCUMENTS

| JP | 2002072779 A | 3/2002 |
| JP | 2009029622 A | 2/2009 |
| JP | 2011037524 A | 2/2011 |

(Continued)

OTHER PUBLICATIONS

JP_2012123125_A_T Machine Translation, Japan, 2012, Tomioka.*

*Primary Examiner* — Clayton E Laballe
*Assistant Examiner* — Victor Verbitsky
(74) *Attorney, Agent, or Firm* — Canon USA, Inc. IP Division

(57) ABSTRACT

An image forming apparatus includes an image forming unit for forming an image on a recording material, a first detection unit including a transmission unit for transmitting an ultrasonic wave and a reception unit for receiving the transmitted ultrasonic wave, first and second conveyance units for conveying the recording material, and a control unit. The first and second conveyance units form a loop on the recording material by conveying the recording material at different speeds. The control unit controls an image forming condition for forming an image on the recording material by the image forming unit, based on the ultrasonic wave received via the recording material in a period in which no loop is formed on the recording material by the first and second conveyance units.

35 Claims, 25 Drawing Sheets

(56) References Cited

FOREIGN PATENT DOCUMENTS

| JP | 2011133524 A |   | 7/2011  |
|----|--------------|---|---------|
| JP | 2012123125 A | * | 6/2012  |
| JP | 2012226138 A |   | 11/2012 |

\* cited by examiner

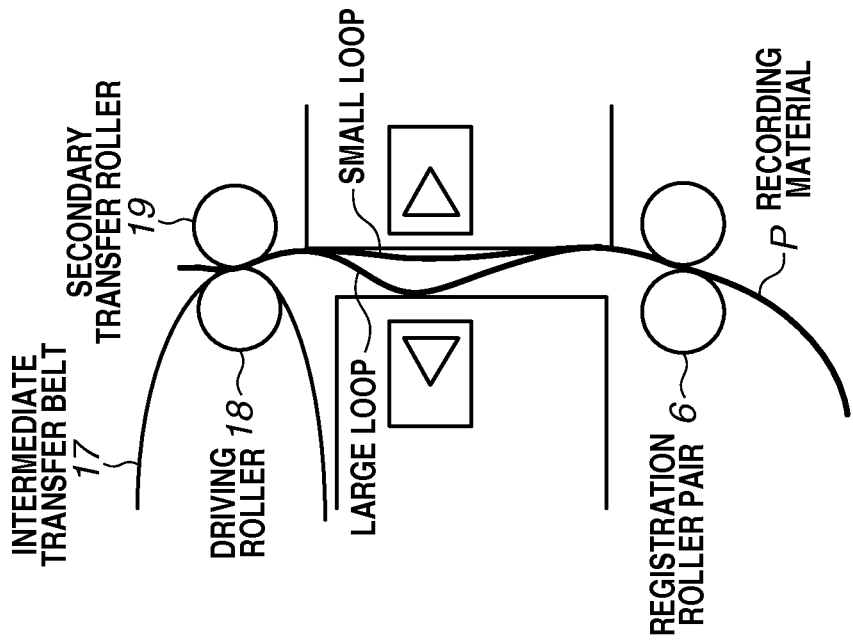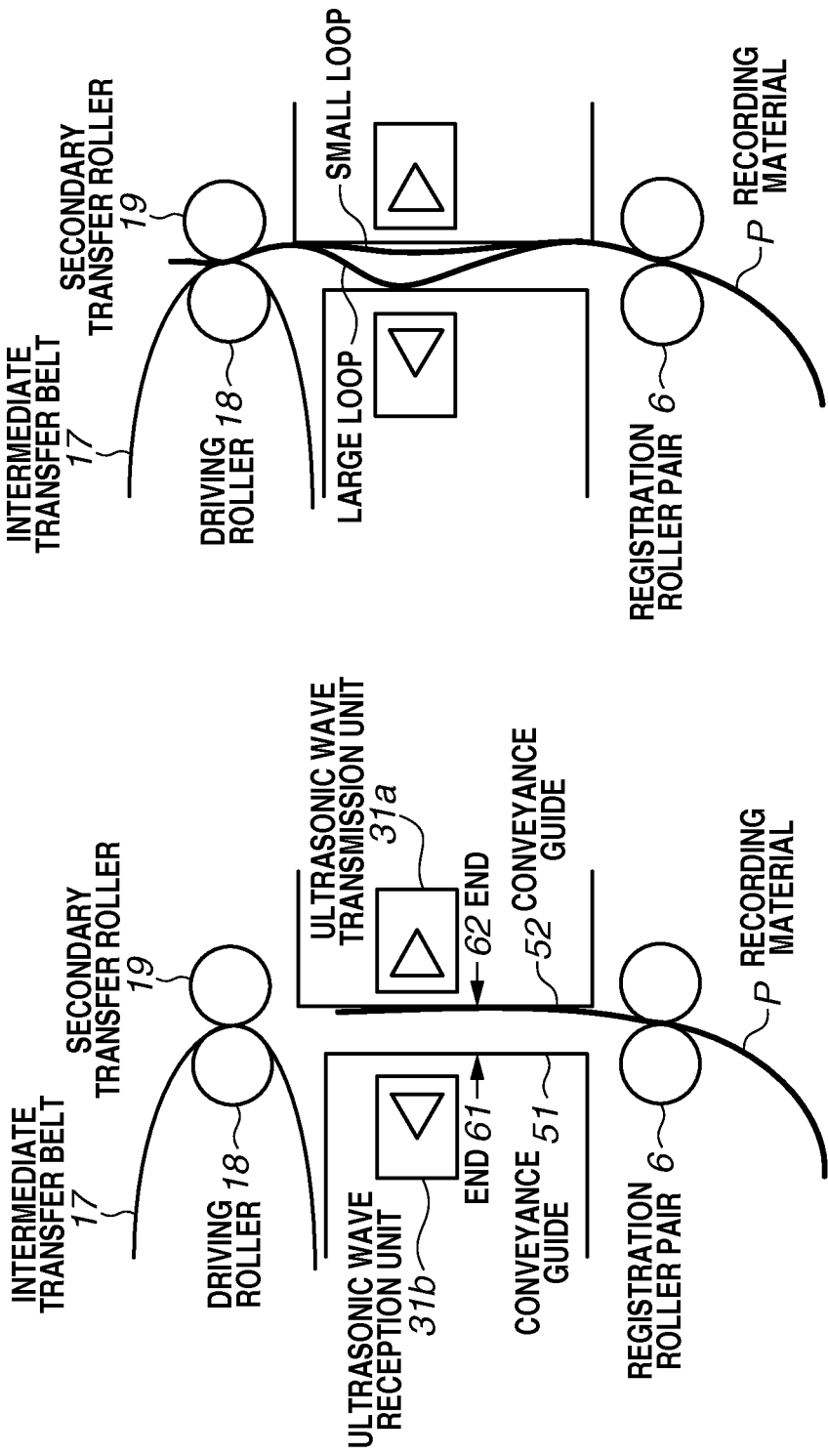

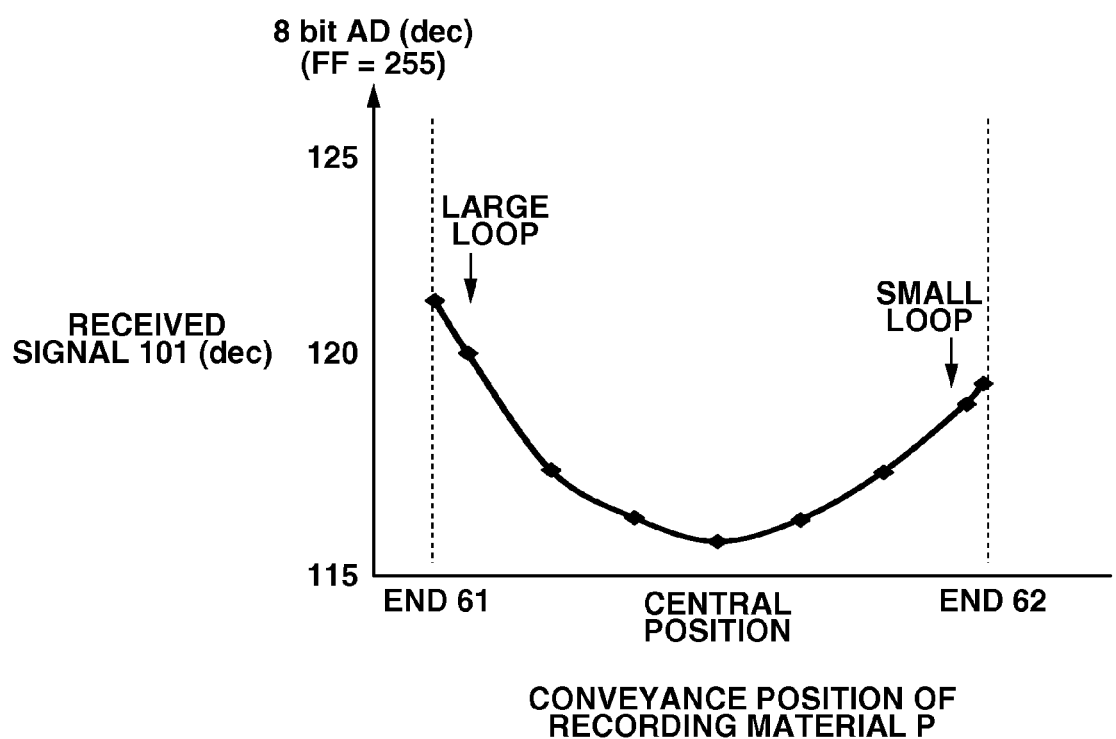

FIG.10

| | CONVEYANCE SPEED OF RECORDING MATERIAL | RECEIVED SIGNAL 101 (dec) [FF = 255] |
|---|---|---|
| (a) | CONSTANT SPEED (1/3 SPEED) | 120 |
| (b) | CONSTANT SPEED (1/1 SPEED) | 120 |
| (c) | CONSTANT SPEED (3/2 SPEED) | 121 |
| (d) | INCREASE SPEED (1/3 SPEED TO 3/2 SPEED) | 120 |
| (e) | DECREASE SPEED (3/2 SPEED TO 1/3 SPEED) | 119 |

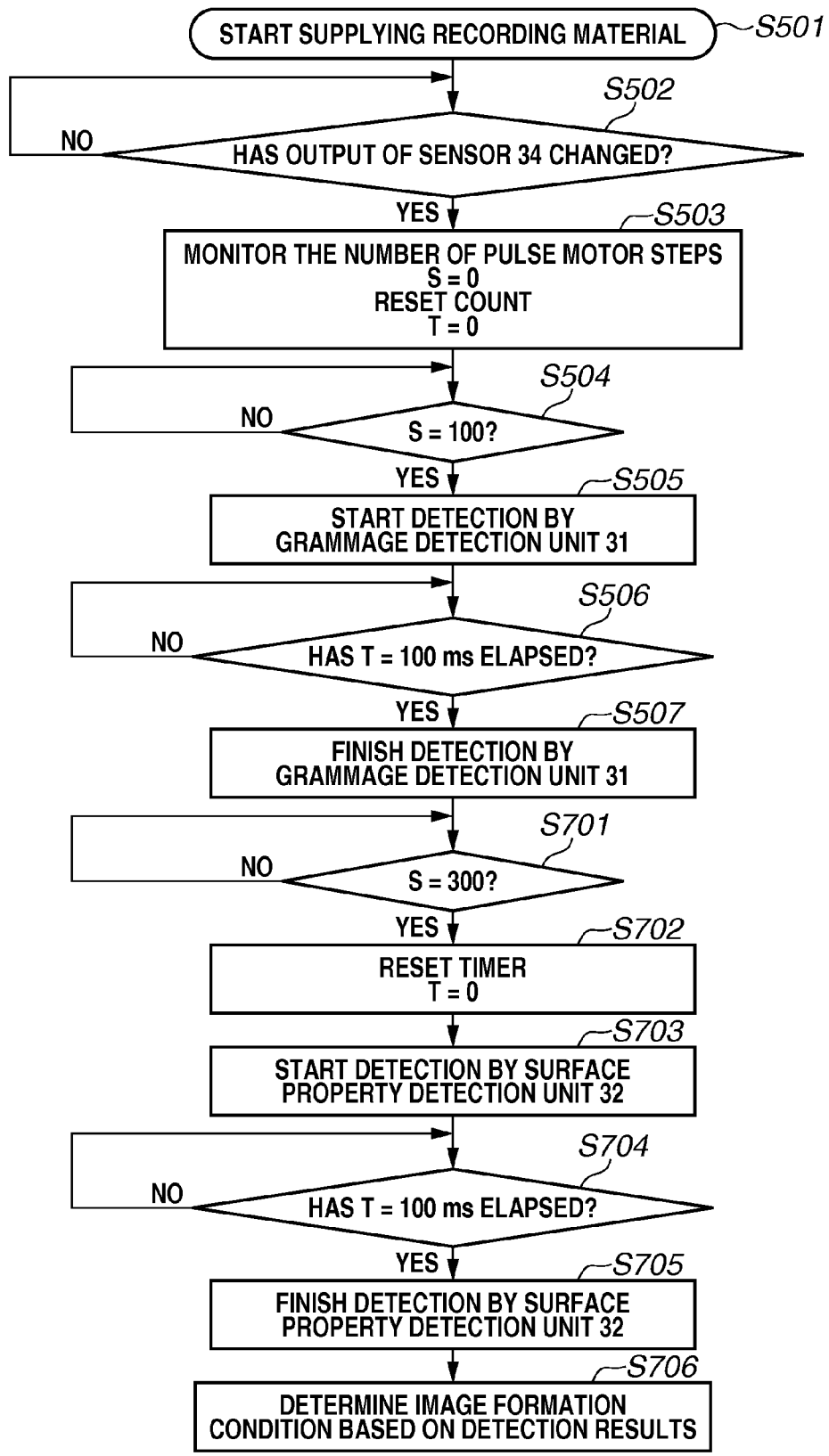

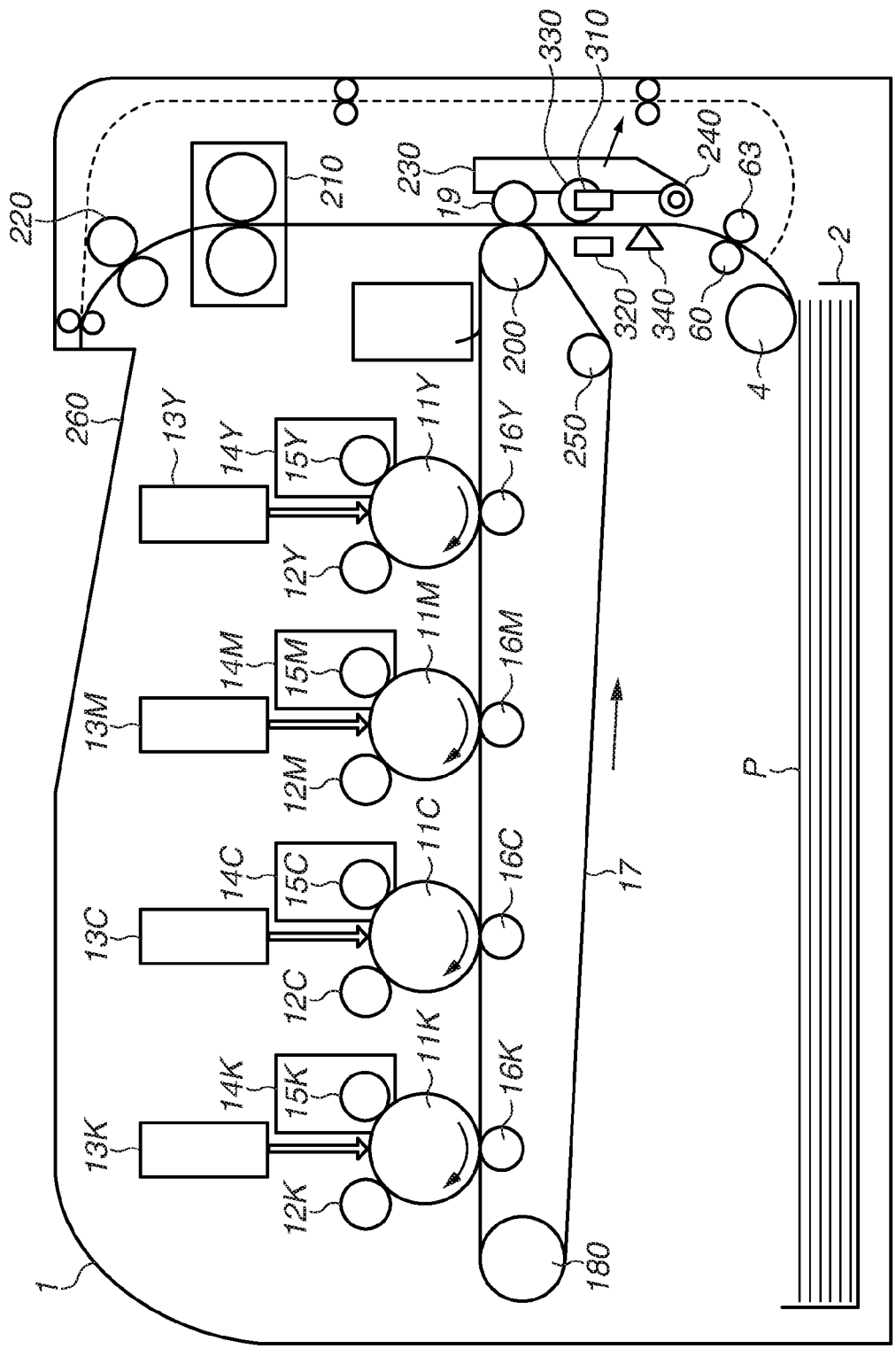

IMAGE FORMING APPARATUS AND RECORDING MATERIAL DETERMINATION UNIT

BACKGROUND OF THE INVENTION

Field of the Invention

The present invention relates to a technique for detecting grammage of a recording material with high accuracy.

Description of the Related Art

Some of conventional image forming apparatuses such as a copier and a printer internally include a sensor for determining the type of recording material. These apparatuses automatically determine the type of recording material and controls transfer and fixing conditions according to the determination result. Examples of the transfer condition include a transfer voltage and a conveyance speed of the recording material during transfer. Examples of the fixing condition include a fixing temperature and a conveyance speed of the recording material at fixing.

Japanese Patent Application Laid-Open No. 2009-29622 discusses an image forming apparatus including an ultrasonic sensor that detects grammage of a recording material by transmitting an ultrasonic wave to the recording material and receiving the ultrasonic wave that has been attenuated after being transmitted through the recording material. The image forming apparatus controls image forming conditions such as transfer and fixing conditions according to the grammage of the recording material that has been detected by the ultrasonic sensor. For feeding back the detection result to the transfer conditions, the ultrasonic sensor is arranged on an upstream side, in a conveyance direction, of a transfer unit that transfers an image onto the recording material.

Meanwhile, there has been a known control of forming a loop on a recording material when an image is transferred onto the recording material by the transfer unit. More specifically, a conveyance unit is positioned on an upstream side of the transfer unit in the conveyance direction of the recording material. The conveyance unit conveys the recording material to the transfer unit at a speed faster than that of the transfer unit, so that a loop is formed on the recording material by the conveyance unit and the transfer unit. The reason for forming a loop on the recording material is that if the recording material is pulled from the conveyance unit while an image is being transferred onto the recording material by the transfer unit, the speed of the recording material may vary during the transfer to cause a problem in the image being transferred. On the other hand, if a loop is formed on the recording material, a significant change may occur in the orientation of the recording material to affect a detection result of the ultrasonic sensor. If the image forming conditions are set based on an erroneous detection result, image quality may be degraded.

SUMMARY OF THE INVENTION

According to an aspect of the present invention, an image forming apparatus includes an image forming unit configured to form an image on a recording material, a first detection unit including a transmission unit configured to transmit an ultrasonic wave and a reception unit configured to receive the transmitted ultrasonic wave, a first conveyance unit arranged on an upstream side of the first detection unit in a conveyance direction of the recording material, and configured to convey the recording material toward a position between the transmission unit and the reception unit, a second conveyance unit arranged on a downstream side of the first detection unit in the conveyance direction, and configured to convey the recording material conveyed by the first conveyance unit, wherein the first conveyance unit and the second conveyance unit form a loop on the recording material by conveying the recording material at different speeds, and a control unit configured to control an image forming condition for forming an image on the recording material by the image forming unit, based on the ultrasonic wave received via the recording material in a period in which no loop is formed on the recording material by the first conveyance unit and the second conveyance unit.

Further features of the present invention will become apparent from the following description of exemplary embodiments with reference to the attached drawings.

BRIEF DESCRIPTION OF THE DRAWINGS

FIGS. 3A and 3B are diagrams illustrating a conveyance position of a recording material according to the first to third exemplary embodiments. FIG. 3C is a diagram illustrating a relationship between a conveyance position of the recording material and a detection result obtained using an ultrasonic wave.

FIG. 10 is a diagram illustrating a relationship between a conveyance speed of a recording material and a detection result obtained using an ultrasonic wave according to the third exemplary embodiment.

FIG. 12 is a flowchart according to the third exemplary embodiment.

FIG. 14 is a configuration diagram of an image forming apparatus according to a fourth exemplary embodiment.

DESCRIPTION OF THE EMBODIMENTS

Hereinafter, first to third exemplary embodiments of the present invention will be described with reference to the drawings. The exemplary embodiments described below are examples and not intended to limit the scope of the present invention.

Figure 1:
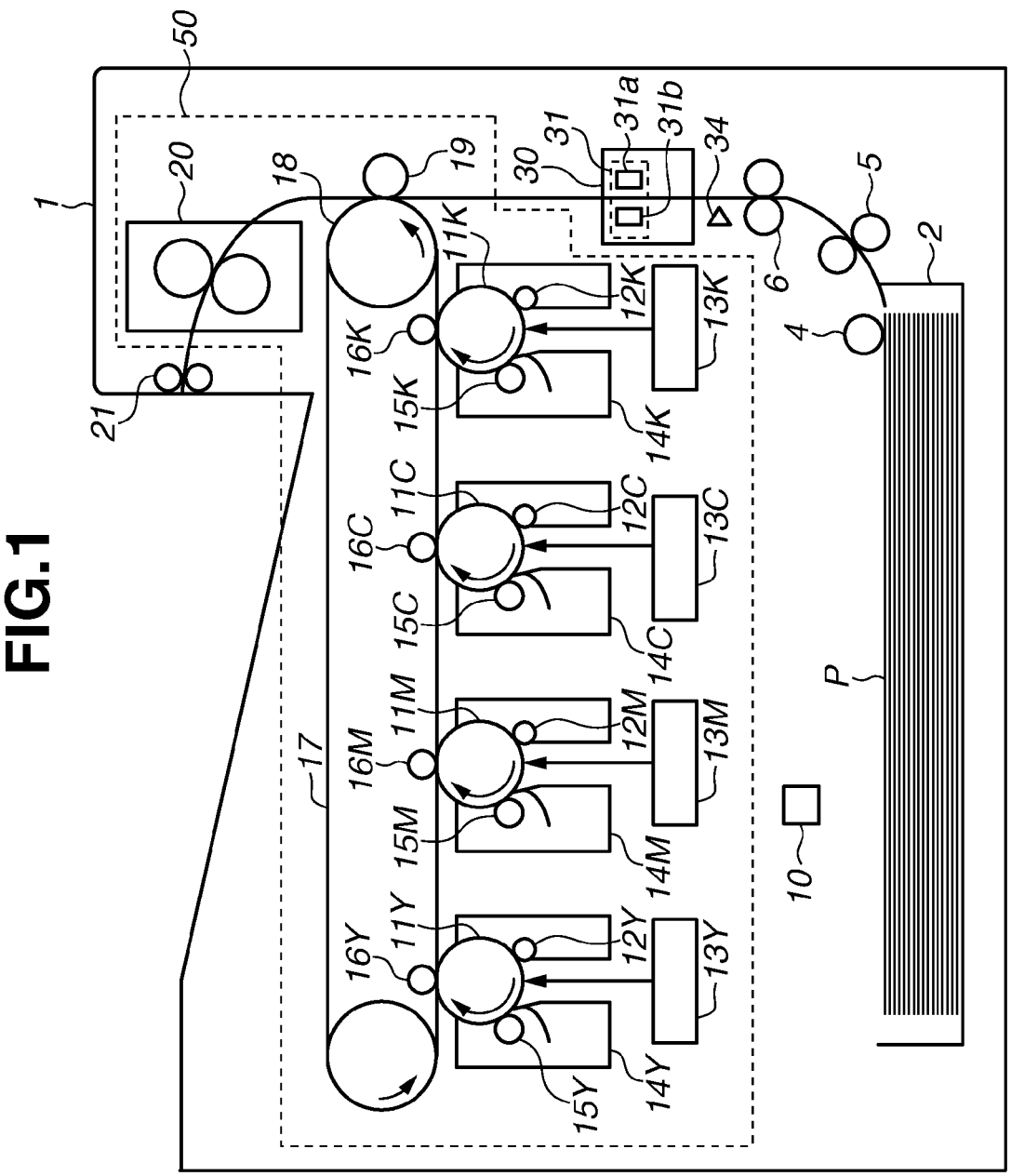
FIG. 1 is a configuration diagram of an image forming apparatus according to first to third exemplary embodiments.

An outline of an electrophotographic image forming apparatus to which the first exemplary embodiment is applicable will be described below. FIG. 1 is a schematic configuration diagram of an image forming apparatus 1 that employs an intermediate transfer belt 17 and has an image forming unit 50 for forming an image on a recording material P.

The image forming apparatus 1 is a tandem type color laser beam printer and configured to be able to output a color image by superimposing four color toners as developers including yellow (Y), magenta (M), cyan C, and black (K). A cassette 2, as an example of a storage unit, stores the recording material P. The image forming apparatus 1 includes a supply roller (sheet feeding roller) 4, a conveyance roller pair 5, and a registration roller pair 6. The supply roller 4 supplies the recording material P from the cassette 2. The conveyance roller pair 5 conveys the recording material P supplied from the supply roller 4. A registration sensor 34 is provided near the registration roller pair 6. The registration sensor 34 is an example of a monitoring unit that detects front and rear ends of the recording material P and monitors the position of the front end of the recording material P.

Photosensitive drums 11 (11Y, 11M, 11C, and 11K) bear toners of respective colors. Charging rollers (charging units) 12 (12Y, 12M, 12C, and 12K) uniformly charge the respective photosensitive drums 11 to a predetermined potential. Laser scanners (exposure units) 13 (13Y, 13M, 13C, and 13K) correspond to the respective colors. Process cartridges (development units) 14 (14Y, 14M, 14C, and 14K) visualize electrostatic latent images formed on the respective photosensitive drums 11 by the scanners 13. Developing rollers 15 (15Y, 15M, 15C, and 15K) feed the toner in the respective cartridges 14 to the respective photosensitive drums 11. Primary transfer rollers 16 (16Y, 16M, 16C, and 16K) primarily transfer the images formed on the respective photosensitive drums 11, onto the intermediate transfer belt 17. The intermediate transfer belt 17 is driven by a driving roller 18 to rotate. A secondary transfer roller 19 transfers the images formed on the intermediate transfer belt 17, onto the recording material P. The rollers 18 and 19 form a nip portion. The images formed on the intermediate transfer belt 17 are transferred onto the recording material P while the recording material P is being nipped and conveyed at the nip portion. These are an example of a transfer unit that secondarily transfers the images onto the recording material P. A fixing device 20 is an example of a fixing unit for melting and fixing the toner images secondarily transferred onto the recording material P, while conveying the recording material P. The above-described components from the photosensitive drums 11 to the fixing device 20 constitute an example of the image forming unit 50.

A discharge roller 21 discharges the recording material P, on which the toner images have been fixed by the fixing device 20, to the outside of the image forming apparatus 1. The roller 4, the roller pairs 5 and 6, the rollers 18 and 19, the fixing device 20, and the roller 21 that are arranged along a conveyance path of the recording material P and a motor (not illustrated) for driving these components constitute an example of a conveyance unit that conveys the recording material P. A recording material determination unit 30 determines the type of the conveyed recording material P. The recording material determination unit 30 has a grammage detection unit 31 that detects grammage of the recording material P. The grammage detection unit 31 includes an ultrasonic wave transmission unit 31a and an ultrasonic wave reception unit 31b. The recording material determination unit 30 determines the type of recording material P according to the grammage detected by the grammage detection unit 31. A control unit 10 includes a micro processing unit (MPU) (not illustrated) including a central processing unit (CPU) (not illustrated) or the like, and has a function of controlling the image forming apparatus 1. The control unit 10 controls an electrophotographic process, and also serves as a determination unit that determines the type of recording material P based on the information detected by the recording material determination unit 30. The control unit 10 determines a print mode according to the determined type of recording material P, and controls various image forming conditions. Herein, examples of image forming conditions include a conveyance speed of the recording material P, a value of a voltage to be applied to the rollers 16 and 19, and a temperature at which the fixing device 20 fixes the images onto the recording material P. Furthermore, the control unit 10 may control, as an image forming condition, rotation speeds of the rollers 16 and 19 at which the images are transferred. Furthermore, the control unit 10 may control, as an image forming condition, the rotation speed of a fixing roller of the fixing device 20 at which the images are fixed.

Figure 2:
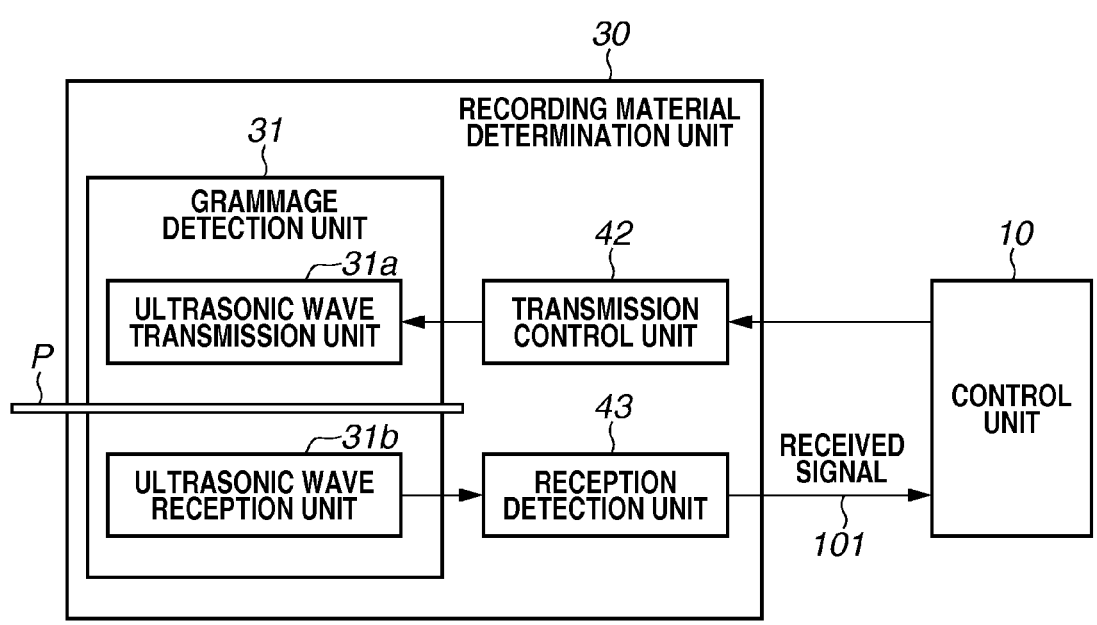
FIG. 2 is a block diagram related to a grammage detection unit of a recording material determination unit according to the first to third exemplary embodiments.

The recording material determination unit 30 that determines the type of recording material P according to the present exemplary embodiment will be described in detail with reference to FIG. 2. FIG. 2 is a block diagram of the recording material determination unit 30 including the grammage detection unit 31.

The grammage detection unit 31 in FIG. 2 includes the transmission unit 31a that transmits an ultrasonic wave and the reception unit 31b that receives the ultrasonic wave. The transmission unit 31a and the reception unit 31b are arranged facing each other. When the recording material P is conveyed to a position between the transmission unit 31a and the reception unit 31*b*, the control unit 10 outputs a signal for starting transmission of an ultrasonic wave, to a transmission control unit 42. Herein, the position between the transmission unit 31*a* and the reception unit 31*b* (a detection position to be detected by the grammage detection unit 31) is a position through which the ultrasonic wave transmitted from the transmission unit 31*a* passes. The transmission unit 31*a* transmits an ultrasonic wave of a specific frequency to the recording material P according to the control of the transmission control unit 42. The reception unit 31*b* has a function of receiving the ultrasonic wave transmitted through the recording material P (via the recording material P). A reception detection unit 43 outputs a peak value of a signal output according to the ultrasonic wave received by the reception unit 31*b*, to the control unit 10 as a received signal 101. The control unit 10 detects grammage of the recording material P based on the received signal 101. When the detection result is obtained, the control unit 10 outputs to the transmission control unit 42 a signal for stopping transmission of the ultrasonic wave. For example, when the detected grammage of the recording material P is small, the control unit 10 determines that the type of recording material P is thin paper. When the detected grammage of the recording material P is large, the control unit 10 determines that the type of recording material P is thick paper.

In the ultrasonic wave transmitted through the recording material P, a peak value in a waveform attenuates according to the grammage of the recording material P. For example, when the recording material P has small grammage (thin paper), the peak value of the ultrasonic wave is large, and when the recording material P has large grammage (thick paper), the peak value of the ultrasonic wave is small. If the control unit 10 sets the fixing temperature of the fixing device 20 appropriately according to the detected grammage, the following effects are achieved. For example, for the recording material P with small grammage such as thin paper, setting the fixing temperature at low temperature decreases the required power. On the contrary, for the recording material P with large grammage such as thick paper, setting the fixing temperature at high temperature or setting the conveyance speed of the recording material P at slow speed improves the fixability. In this manner, the control unit 10 controls the image forming conditions of the image forming apparatus 1 based on the detection result of the grammage. In addition, the control unit 10 may directly control the image forming conditions of the image forming apparatus 1 based on the value of the signal 101, without detecting grammage of the recording material P.

Next, a period for which the grammage detection unit 31 detects the recording material P will be described. FIGS. 3A and 3B illustrate conveyance positions of the recording material P between the roller pair 6 serving as a conveyance unit, and the roller 19 serving as a transfer unit. As illustrated in FIG. 3A, a loop is not formed on the recording material P before the front end of the recording material P (the end on the downstream side in the conveyance direction of the recording material P) reaches the roller 19 (nip portion between the rollers 18 and 19). At this time, the recording material P is conveyed by the roller pair 6 and the recording material P is pressed against a conveyance guide 52, so that the conveyance position of the recording material P becomes stable. On the other hand, as illustrated in FIG. 3B, a loop is formed on the recording material P after the front end of the recording material P has reached the roller 19. When the recording material P is conveyed by both the roller pair 6 and the roller 19, if the recording material P is pulled by the roller 19 on the downstream side, the speed of the recording material P may vary during transfer to cause deterioration in image quality. Accordingly, by making the rotation speed of the roller pair 6 faster than the speed of the roller 19, a loop is formed on the recording material P to suppress the pulling. The roller pair 6 and the roller 19, however, have a variation in product tolerance and abrasion due to a secular change, so that the roller diameter changes. Thus, the same loop is not always formed. Therefore, as illustrated in FIG. 3B, a large loop is formed in one case, and a small loop is formed in another case.

FIG. 3C is a graph illustrating the relationship between the conveyance position of the recording material P and the signal 101 output by the reception detection unit 43. The value of the signal 101 is smaller in a case where the recording material P is conveyed to a position close to a central position between the conveyance guides 51 and 52, as compared with a case where the recording material P is conveyed to a position (an end 61) near the conveyance guide 51 or a position (an end 62) near the guide 52. Accordingly, when the loop is formed within a conveyance path, the conveyance position of the recording material P varies, leading to a variation in the detection result of the grammage detection unit 31.

Considering the above, a desirable detection period of the grammage detection unit 31 is a period in which the conveyance position of the recording material P is stable. That is, the period is a period in which no loop is formed on the recording material P. The present exemplary embodiment describes, as an example, a case where detection is performed in the period from a time point at which the front end of the recording material P has passed through a position between the transmission unit 31*a* and the reception unit 31*b*, to a time point at which the front end of the recording material P reaches the roller 19. The period is not limited to the above period as long as the conveyance position of the recording material P is stable and no loop is formed on the recording material P. For example, the period may be a period from a time point at which the rear end of the recording material P (end on the upstream side in the conveyance direction of the recording material P) has passed through the roller pair 6 to a time point at which the rear end of the recording material P reaches the position between the transmission unit 31*a* and the reception unit 31*b*. Even in this case, it is possible to control the temperature at which the fixing device 20 fixes an image onto the recording material P, and to control the rotation speed of the fixing roller of the fixing device 20. Accordingly, the period is a period in which the recording material P is conveyed by either one of the roller pair 6 and the roller 19 and is not conveyed by the other one.

Figure 4:
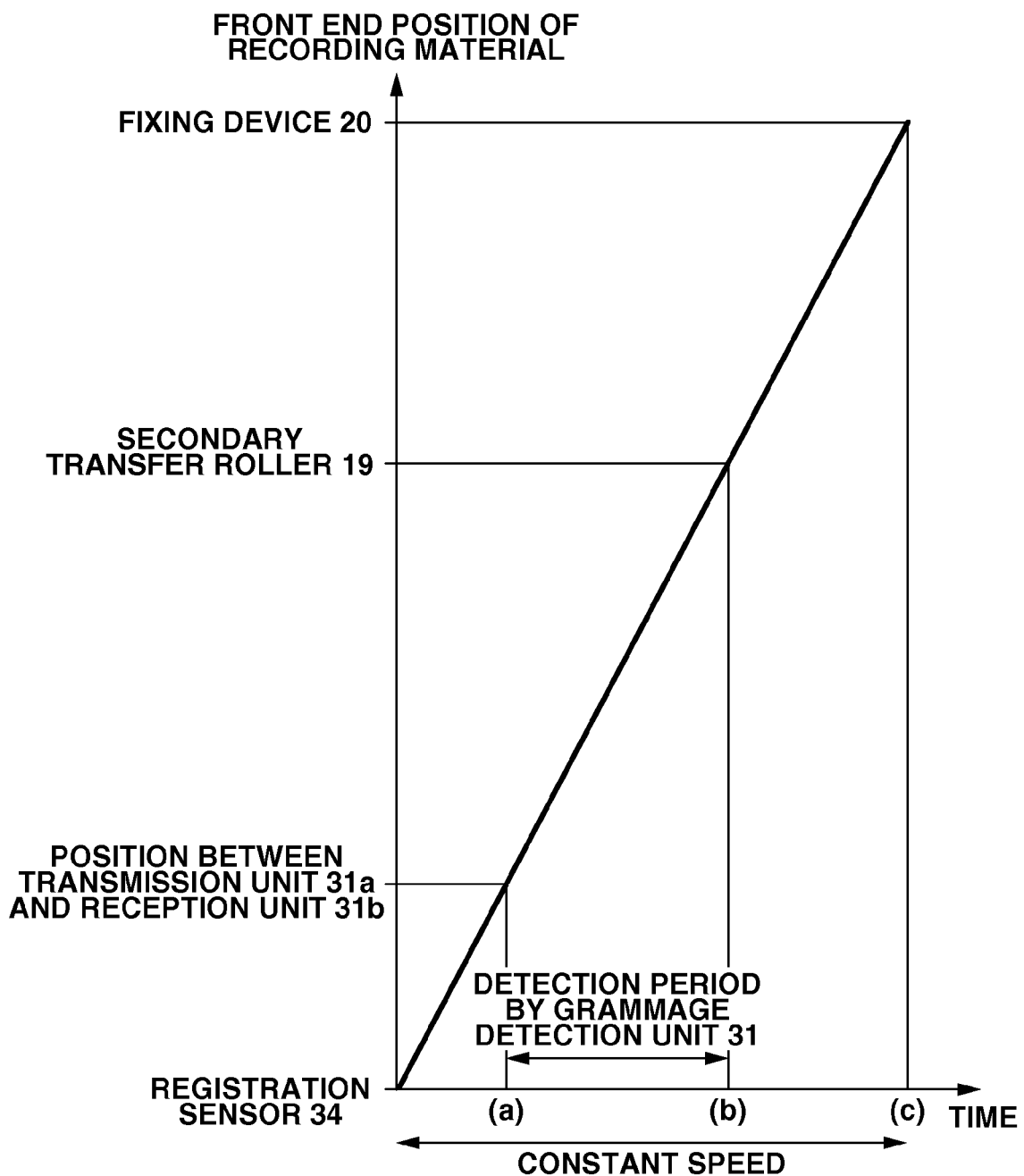
FIG. 4 is a timing chart according to the first exemplary embodiment.

The detection period of the grammage detection unit 31 according to the present exemplary embodiment will be described with reference to a timing chart in FIG. 4. The timing chart in FIG. 4 illustrates the period from a time point at which the front end of the recording material P has passed through the registration sensor 34 to a time point at which the front end reaches the fixing device 20. In the present exemplary embodiment, the recording material P is conveyed at a constant speed in this period. As described above, a desirable detection period of the grammage detection unit 31 is the period in which the conveyance position of the recording material P is stable. This period corresponds to the period from the time point at which the front end of the recording material P has passed through the position between the transmission unit 31*a* and the reception unit 31*b*, to the time point at which the front end of the recording material P reaches the roller 19. In the timing chart in FIG. 4, the period corresponds to a period from timings (a) to (b) in FIG. 4. Herein, the timing (a) in FIG. 4 indicates a timing at which the front end of the recording material P has reached the position between the transmission unit 31*a* and the reception unit 31*b* (detection position to be detected by the grammage detection unit 31). The timing (b) in FIG. 4 indicates a timing at which the front end of the recording material P has reached the roller 19. A timing (c) in FIG. 4 indicates the timing at which the front end of the recording material P has reached the fixing device 20.

Next, a method for monitoring the front end position of the recording material P and a positional relationship in arrangement in a conveyance system will be described. In the present exemplary embodiment, the front end position of the recording material P is monitored using the sensor 34, a pulse motor (not illustrated), and the control unit 10. The number of steps of the pulse motor has a proportional relationship with the rotation distance. Therefore, the distance for which the recording material P has advanced after passing the roller pair 6 can be estimated from the counted number of steps. The present exemplary embodiment assumes that 100 steps are required before the front end of the recording material P reaches the position between the transmission unit 31*a* and the reception unit 31*b* and that 300 steps are required before the front end of the recording material P reaches the roller 19, with reference to the position where the front end of the recording material P has passed through the roller pair 6. In addition, the present exemplary embodiment assumes that 500 steps are required before the front end of the recording material P reaches the fixing device 20. These numbers of steps described above are only examples. The number is calculated by the control unit 10 based on diameters or the like of the pulse motor and the roller pair 6 that are to be used. In addition, the motor is not limited to the pulse motor. Herein, a method using the number of steps of the pulse motor has been described as a method for monitoring the position of the front end of the recording material P. However, the method is not limited to this. It is only required to be able to determine whether the front end of the recording material P has reached a position between the transmission unit 31*a* and the reception unit 31*b*. Therefore, it is also possible to perform management by time, in which measurement starts after a predetermined time has elapsed from the time point at which an output change has occurred in the sensor 34. Herein, detection by the grammage detection unit 31 is assumed to be performed for 100 ms. The detection period is, however, not limited to 100 ms because it is only required that the detection is completed before the front end of the recording material P reaches the roller 19.

Figure 5:
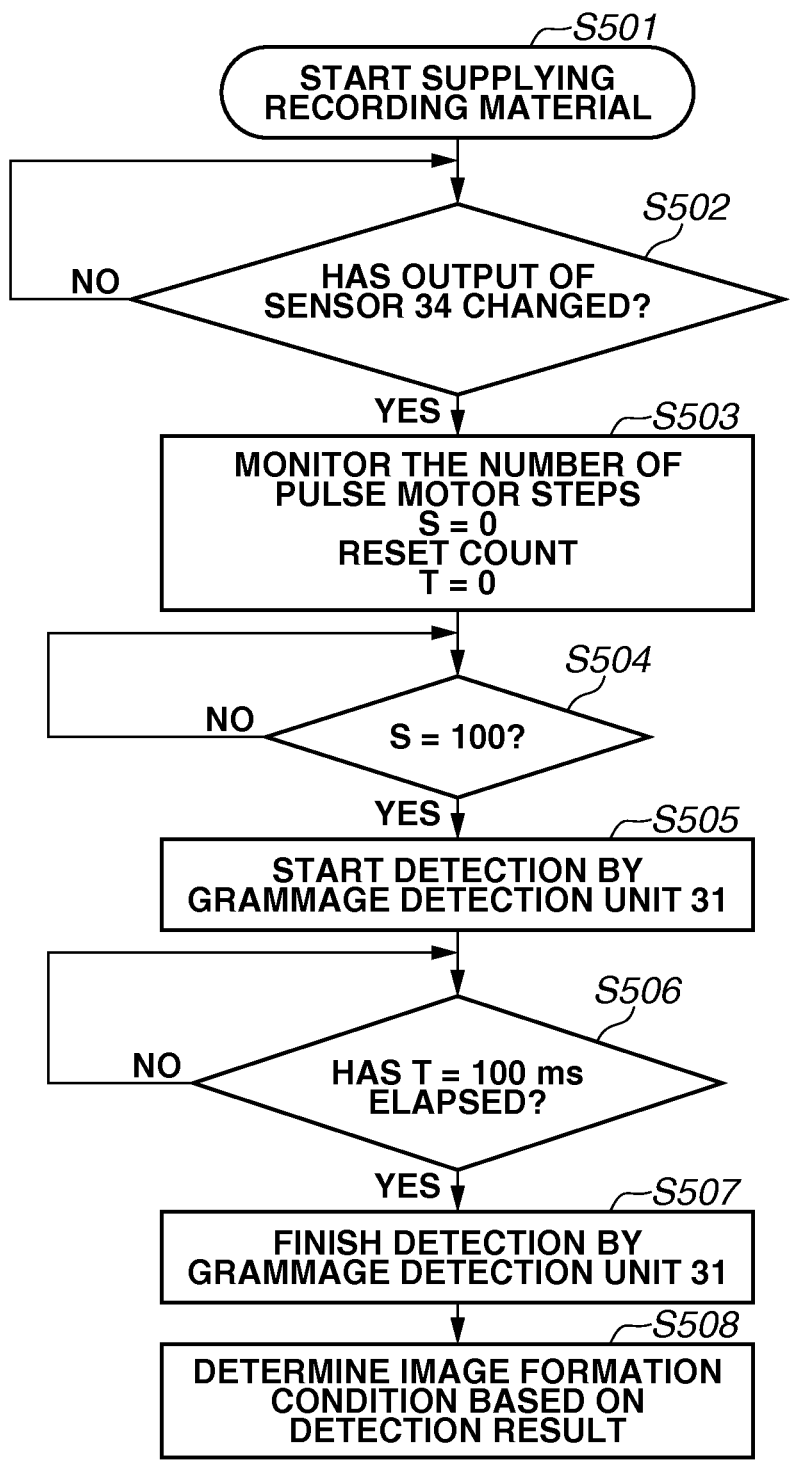
FIG. 5 is a flowchart according to the first exemplary embodiment.

A control sequence of the control unit 10 according to the present exemplary embodiment will be described with reference to a flowchart in FIG. 5. Control based on the flowchart in FIG. 5 is executed by the control unit 10 based on a program stored in a read-only memory (ROM) (not illustrated) or the like. After receiving a print instruction, in step S501, the control unit 10 first instructs supply of the recording material P from the cassette 2 and start of an image forming operation. According to the instruction, the recording material P is supplied by the roller 4 from the cassette 2. Thereafter, the recording material P passes through the roller pairs 5 and 6, and an output of the sensor 34 changes at a timing at which the front end of the recording material P passes through the roller pair 6. In step S502, it is determined whether the output of the sensor 34 has changed. If the output has changed (YES in step S502), then in step S503, the control unit 10 starts, from the output change timing, counting the number of steps of the pulse motor (not illustrated). In step S503, a timer count inside the control unit 10 is also reset. In step S504, it is determined whether 100 steps have been counted from a timing (T=0) at which the output of the sensor 34 has changed. If 100 steps have been counted (YES in step S504), the control unit 10 determines that the front end of the recording material P has reached the position between the transmission unit 31*a* and the reception unit 31*b*, and then in step S505, instructs start of a detection operation by the grammage detection unit 31. In step S506, it is determined whether the detection by the grammage detection unit 31 has been performed for 100 ms. If the detection has been performed for 100 ms (YES in step S506), then in step S507, the detection finishes. In step S508, the control unit 10 determines the type of recording material P based on a detection result obtained by the grammage detection unit 31, and determines image forming conditions according to the determined type. The processing then finishes.

Furthermore, for obtaining more accurate detection results, the grammage detection unit 31 does not perform detection after the front end of the recording material P has reached the roller 19, due to the above-described reason. The description has been given of the case where the recording material P is supplied from the cassette 2. Alternatively, the recording material P may be supplied from an optional device (not illustrated) that is detachably attached the image forming apparatus 1.

According to the present exemplary embodiment, the above-described configuration and operation can bring about the following effects. Performing detection in a period in which the conveyance position of the recording material P is stable can improve the detection accuracy of grammage of the recording material P. Furthermore, the improvement in the detection accuracy of grammage of the recording material P enables appropriate print mode setting, leading to enhanced quality of an image to be formed.

In the present exemplary embodiment, there can be considered a configuration of separately providing, between the conveyance unit and the transfer unit, a loop sensor for detecting an amount of loop of the recording material P. It is estimated that, if the amount of loop of the recording material P is maintained at a predetermined value using the loop sensor, and the detection by the grammage detection unit 31 is performed in this state, theoretically, the same detection result is obtained as long as the recording material P has the same grammage. This configuration, however, requires an additional loop sensor, leading to an increase in costs. According to the present exemplary embodiment, the grammage of the recording material P can be detected without adding a loop sensor, namely, without extra costs. The description herein is not intended to prohibit the addition of a loop sensor in the present exemplary embodiment.

In a second exemplary embodiment, the description will be given of a configuration in which the recording material determination unit 30 includes a surface property detection unit 32 that detects the surface property of the recording material P, in addition to the grammage detection unit 31 that detects the grammage of the recording material P. Description on main parts is similar to that in the first exemplary embodiment. Herein, therefore, only the parts different from the first exemplary embodiment will be described.

Figure 6:
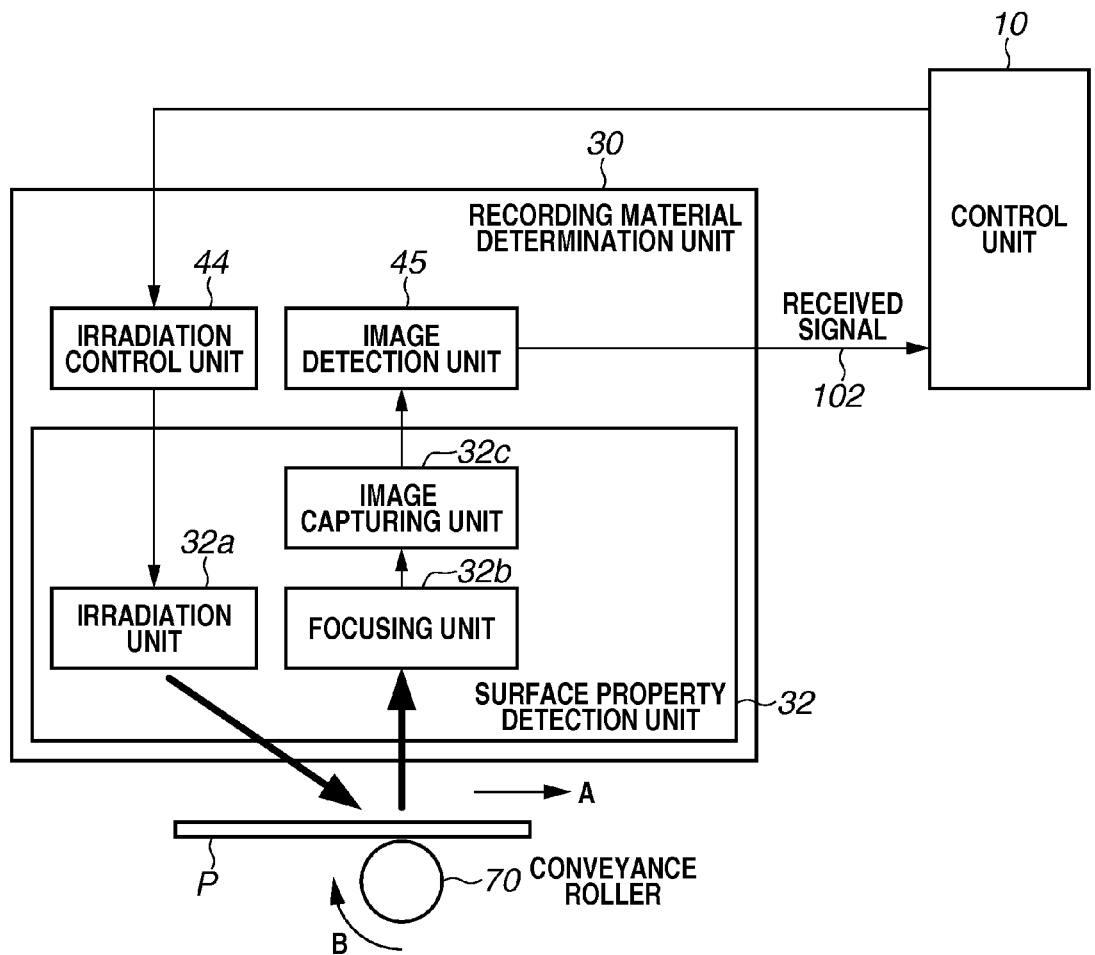
FIG. 6 is a block diagram related to a surface property detection unit according to the second and third exemplary embodiments.

Hereinafter, the recording material determination unit 30 that determines the type of recording material P according to the present exemplary embodiment will be described in detail. The recording material determination unit 30 has the grammage detection unit 31 as illustrated in FIG. 2, similarly to the first exemplary embodiment. The recording material determination unit 30 further includes the surface property detection unit 32. FIG. 6 is a block diagram of the recording material determination unit 30 including the surface property detection unit 32.

The surface property detection unit 32 illustrated in FIG. 6 includes an irradiation unit 32*a*, a focusing unit 32*b*, and an image capturing unit 32*c*. The irradiation unit 32*a* irradiates a surface of the recording material P with light. The focusing unit 32*b* forms an image of reflected light emitted from the irradiation unit 32*a* and reflected on the surface of the recording material P (via the recording material P). The image capturing unit 32*c* is a light receiving unit that receives the light that has been imaged by the focusing unit 32*b*, and captures the received light as an image. When the recording material P is conveyed at a constant speed to a detection position to be detected by the surface property detection unit 32, the control unit 10 outputs to an irradiation control unit 44 a signal for starting emission of light. Herein, the detection position to be detected by the surface property detection unit 32 is a position to which light can be emitted from the irradiation unit 32*a*. The irradiation unit 32*a* irradiates the surface of the recording material P with light according to control of the irradiation control unit 44. For adjusting a focal length to the recording material P, the recording material P is configured to be pressed, on a back surface thereof, by a component such as a conveyance roller 70, so that the conveyance position is fixed. The roller 70 is an example of a contact member that contacts the recording material P irradiated with light, on a surface opposite to the surface irradiated with light. The roller 70 holds, from the back surface, a region irradiated with light. The recording material P is conveyed in the direction indicated by an arrow A in FIG. 6. The roller 70 rotates in the direction indicated by an arrow B, along with the conveyance of the recording material P. The light emitted onto the recording material P is captured as an image by the image capturing unit 32*c* via the focusing unit 32*b*. In the present exemplary embodiment, a line sensor extending in the width direction of the recording material P is used as the image capturing unit 32*c*. By using a line sensor, an image can be captured while the recording material P is being conveyed. The captured image is an image of the surface of the recording material P and is output to an image detection unit 45. The image detection unit 45 outputs a received signal 102 to the control unit 10 according to image data. Herein, the received signal 102 can be, for example, information related to the surface property, such as a difference between the maximum and minimum density values included in the image data. The control unit 10 detects the surface property of the recording material P based on the received signal 102. After the detection result is obtained, the control unit 10 outputs to the irradiation control unit 44 a signal for stopping emission of light. When the detected surface of the recording material P is rough, for example, the control unit 10 determines that the type of recording material P is rough paper. When the surface of the recording material P is smooth, the control unit 10 determines that the type of recording material P is coated paper.

The captured image varies according to the difference in the surface property (unevenness) of the recording material P. When the recording material P is rough paper having a rough surface, for example, an obtained image has a high percentage of shadow due to the emitted light. On the other hand, if the recording material P is coated paper having a smooth surface, an obtained image has less shadow. The recording material P such as coated paper having a smooth surface property has a relatively low resistance value and requires higher transfer current and higher transfer voltage for transferring a toner image, as compared with the case of the rough recording material P such as rough paper. Therefore, controlling by the control unit 10 the transfer current and transfer voltage according to a detection result of the surface property is also effective for enhancing image quality. In this manner, the control unit 10 controls the image forming conditions of the image forming apparatus 1 based on the detection result of the surface property. In addition, the control unit 10 may directly control the image forming conditions of the image forming apparatus 1 based on the value of the signal 102, without detecting the surface property of the recording material P.

Figure 7:
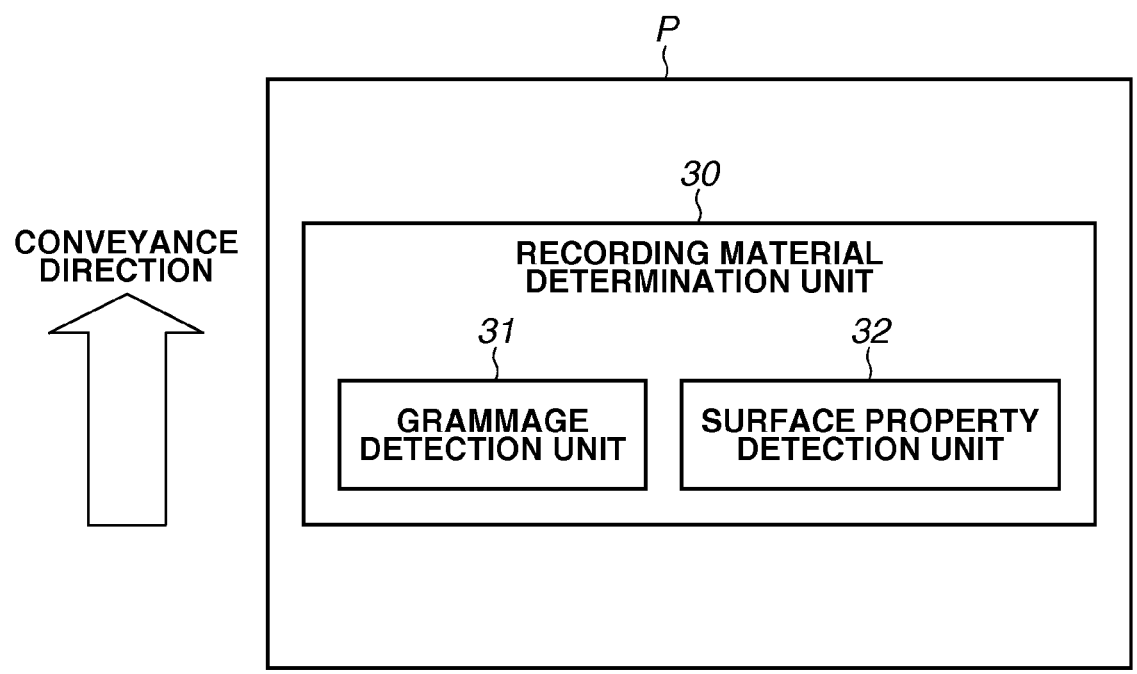
FIG. 7 is a diagram illustrating an arrangement relationship between the grammage detection unit and the surface property detection unit according to the second exemplary embodiment.

Next, a period for which the surface property detection unit 32 detects the recording material P will be described. In the present exemplary embodiment, as illustrated in FIG. 7, the detection units 31 and 32 are arranged side by side in a direction orthogonal to a conveyance direction of the recording material P (width direction of the recording material P). In addition, since the recording material P is held by a component such as the roller 70 from the back surface as described above, the surface property detection unit 32 is not easily influenced by a loop. Meanwhile, for capturing a stable image by the line sensor (the image capturing unit 32*c*), it is desirable that a conveyance speed of the recording material P to be imaged is constant. From the above aspects, a desirable detection period of the surface property detection unit 32 is a period in which the conveyance speed of the recording material P is constant, regardless of presence or absence of a loop.

Figure 8:
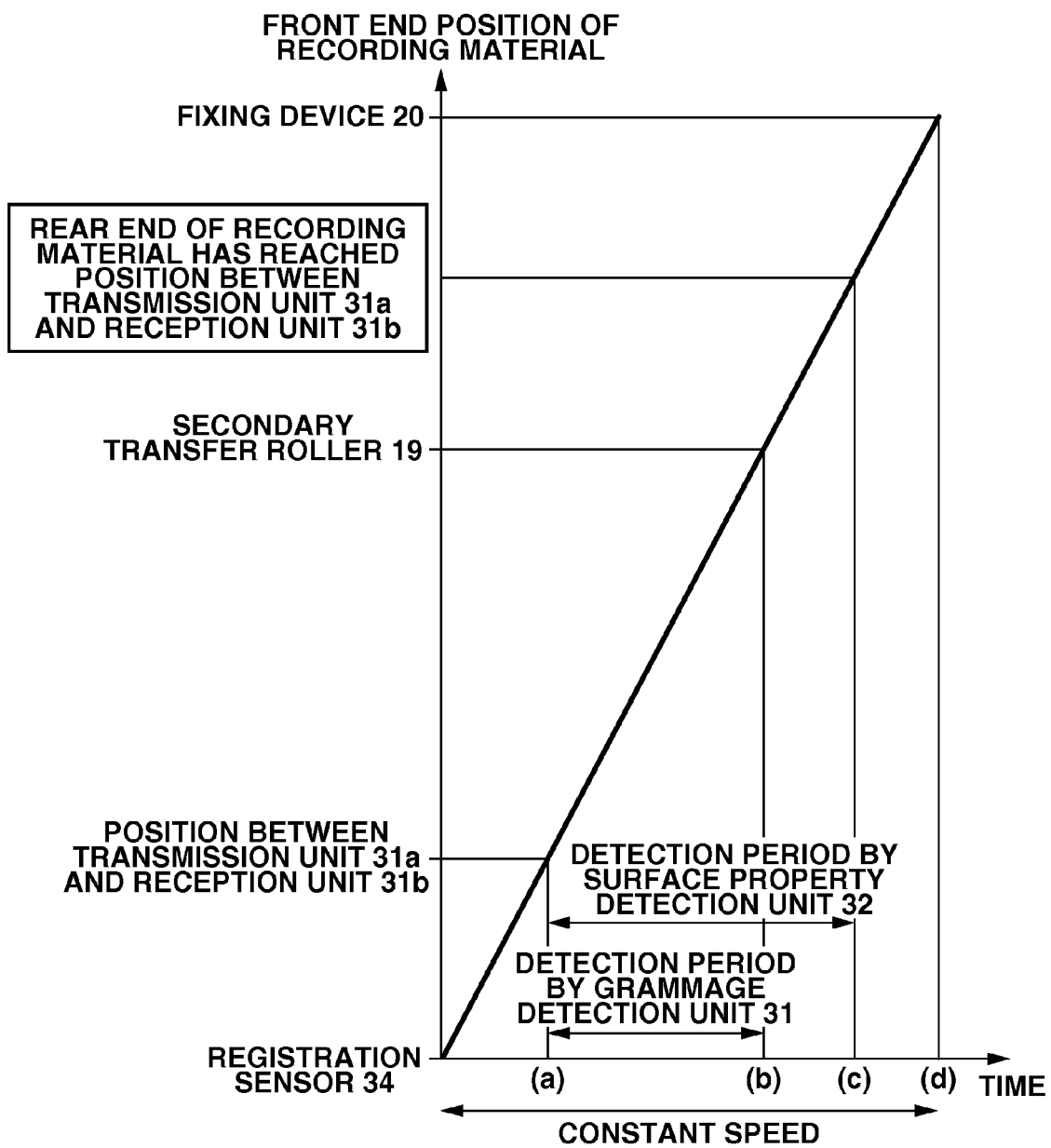
FIG. 8 is a timing chart according to the second exemplary embodiment.

The detection period of the detection units 31 and 32 according to the present exemplary embodiment will be described with reference to a timing chart in FIG. 8. The timing chart in FIG. 8 illustrates a period from a time point at which the front end of the recording material P has passed through the registration sensor 34, to a time point at which the front end reaches the fixing device 20. In the present exemplary embodiment, the recording material P is conveyed at a constant speed in this period. A desirable detection period of the grammage detection unit 31 is a period similar to that in the first exemplary embodiment. The detection period of the surface property detection unit 32 is not particularly specified because the conveyance speed of the recording material P is constant. Thus, the period is only required to be a period in which the recording material P exists at the detection position to be detected by the surface property detection unit 32. In FIG. 8, the position between the transmission unit 31*a* and the reception unit 31*b* (detection position to be detected by the grammage detection unit 31), and the detection position to be detected by the surface property detection unit 32 are assumed to be at substantially the same position in the conveying direction of the recording material P. Therefore, the detection period of the surface property detection unit 32 is set to a period from timings (a) to (c) in FIG. 8. Herein, the timings (a), (b), and (d) in FIG. 8 indicate the same timings as the timings (a), (b), and (c) in FIG. 4, respectively. Herein, the timing (c) in FIG. 8 indicates a timing at which the rear end of the recording material P has reached the position between the transmission unit 31*a* and the reception unit 31*b* (detection position to be detected by the grammage detection unit 31). The period from the timings (a) to (c) in FIG. 8 includes a period in which a loop is formed on the recording material P. In this manner, the conveyance speed of the recording material P temporarily changes during execution of loop control. The change, however, is as small as tolerance and scarcely affects detection accuracy of the surface property detection unit 32. Therefore, in the present exemplary embodiment, the recording material P can be considered to be conveyed at a constant speed during execution of the loop control.

Herein, detection by the grammage detection unit 31 is assumed to be performed for 100 ms. The detection period is, however, not limited to 100 ms because it is only required that the detection finishes before the front end of the recording material P reaches the roller 19. Herein, detection by the surface property detection unit 32 is assumed to be performed for 150 ms. In the present exemplary embodiment, the time taken for the surface property detection unit 32 detecting the recording material P is secured as long time as possible in this manner, so that more image data can be obtained. As a result, the surface property detection accuracy by the surface property detection unit 32 is improved. The detection period is not limited to 150 ms because it is only required that the detection finishes before the rear end of the recording material P reaches the position between the transmission unit 31a and the reception unit 31b. For example, for simplifying the control, the detection by the surface property detection unit 32 may be performed for 100 ms in harmony with the detection time of the grammage detection unit 31.

Figure 9:
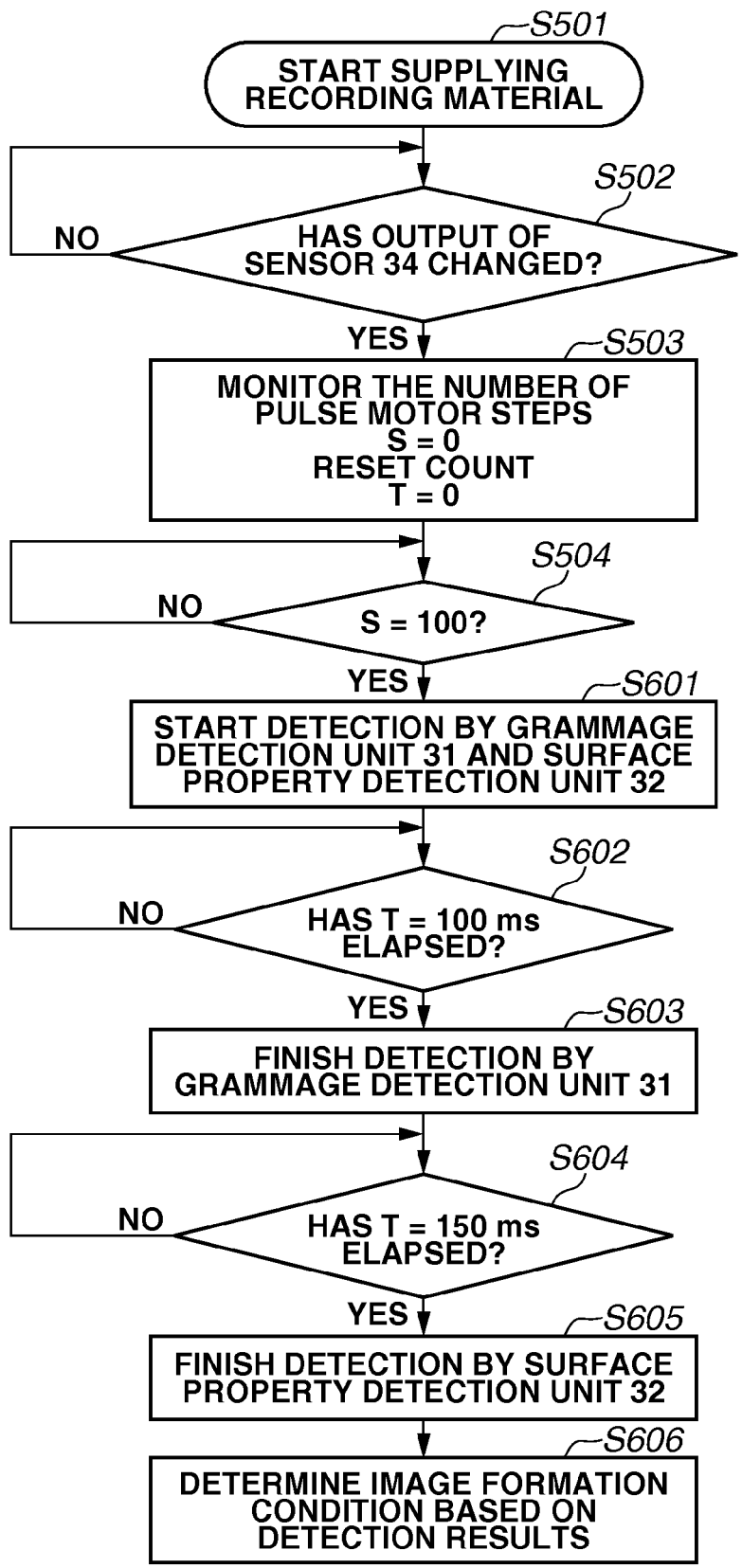
FIG. 9 is a flowchart according to the second exemplary embodiment.

A control sequence of the control unit 10 according to the present exemplary embodiment will be described with reference to a flowchart in FIG. 9. Control based on the flowchart in FIG. 9 is executed by the control unit 10 based on a program stored in a ROM (not illustrated). Control from steps S501 to S504 is performed similarly to the control in FIG. 5. In step S504, it is determined whether 100 steps have been counted from the timing (T=0) at which the output of the sensor 34 has changed. If 100 steps have been counted (YES in step S504), the control unit 10 determines that the front end of the recording material P has reached the position between the transmission unit 31a and the reception unit 31b, and then in step S601, instructs start of detection operations by the detection units 31 and 32. In step S602, it is determined whether the detection by the grammage detection unit 31 has been performed for 100 ms. If the detection has been performed for 100 ms (YES in step S602), then in step S603, the detection by the grammage detection unit 31 finishes. In step S604, it is determined whether the detection by the surface property detection unit 32 has been performed for 150 ms. If the detection has been performed for 150 ms (YES in step S604), then in step S605, the detection by the surface property detection unit 32 finishes. In step S606, the control unit 10 determines the type of recording material P based on the detection results obtained by the detection units 31 and 32, and determines image forming conditions according to the determined type. The processing then finishes.

According to the present exemplary embodiment, the above-described configuration and operation can bring about the following effects in addition to the effects obtained by the first exemplary embodiment. That is, detecting not only the grammage but also the surface property of the recording material P enables more specific determination of the type of recording material P. Furthermore, holding the recording material P by the conveyance roller can suppress the influence from the loop and make detection time by the surface property detection unit 32 longer. This consequently leads to improvement in the detection accuracy of the surface property of the recording material P by the surface property detection unit 32.

In a third exemplary embodiment, the description will be given of the detection periods of the detection units 31 and 32 that are set in a case where the conveyance speed of the recording material P is increased or decreased. Descriptions on main parts are similar to that in the first or second exemplary embodiment. Herein, therefore, the parts different from the first or second exemplary embodiment will be described.

The conveyance speed of the recording material P is increased or decreased for controlling the variation in a sheet interval (distance between the rear end of the preceding sheet and the front end of the succeeding sheet) and for aligning a writing position where an image is secondarily transferred onto the recording material P. This brings about effects including improvement in throughput due to the shortened sheet interval, and increased accuracy of an image forming position on the recording material P.

The relationship between the conveyance speed of the recording material P and the detection result (received signal 101) obtained by the reception detection unit 43 using an ultrasonic wave will be described with reference to FIG. 10. Results (a), (b), and (c) in FIG. 10 indicate measurement results obtained when the roller pair 6 conveys the recording material P at a constant speed and before the front end of the recording material P reaches the roller 19. As seen from the results (a), (b), and (c) in FIG. 10, when the conveyance speed is not changed, there is no substantial difference between the detection results (received signals 101) obtained by the detection unit 43. Meanwhile, results (d) and (e) in FIG. 10 indicate measurement results obtained when the roller pair 6 conveys the recording material P at an increased or decreased speed and before the front end of the recording material P reaches the roller 19. The detection results are substantially equal to the results (a), (b), and (c) in FIG. 10 described above. In this manner, the conveyance position remains stable until the front end of the recording material P reaches the roller 19. Therefore, increasing or decreasing the conveyance speed scarcely affects the detection result. From the above aspects, a desirable detection period of the grammage detection unit 31 is, as described above, the period in which the conveyance position of the recording material P is stable, regardless of increase or decrease in the conveyance speed. On the other hand, a desirable detection period of the surface property detection unit 32 is, as described above, the period in which the conveyance speed of the recording material P is constant.

Figure 11:
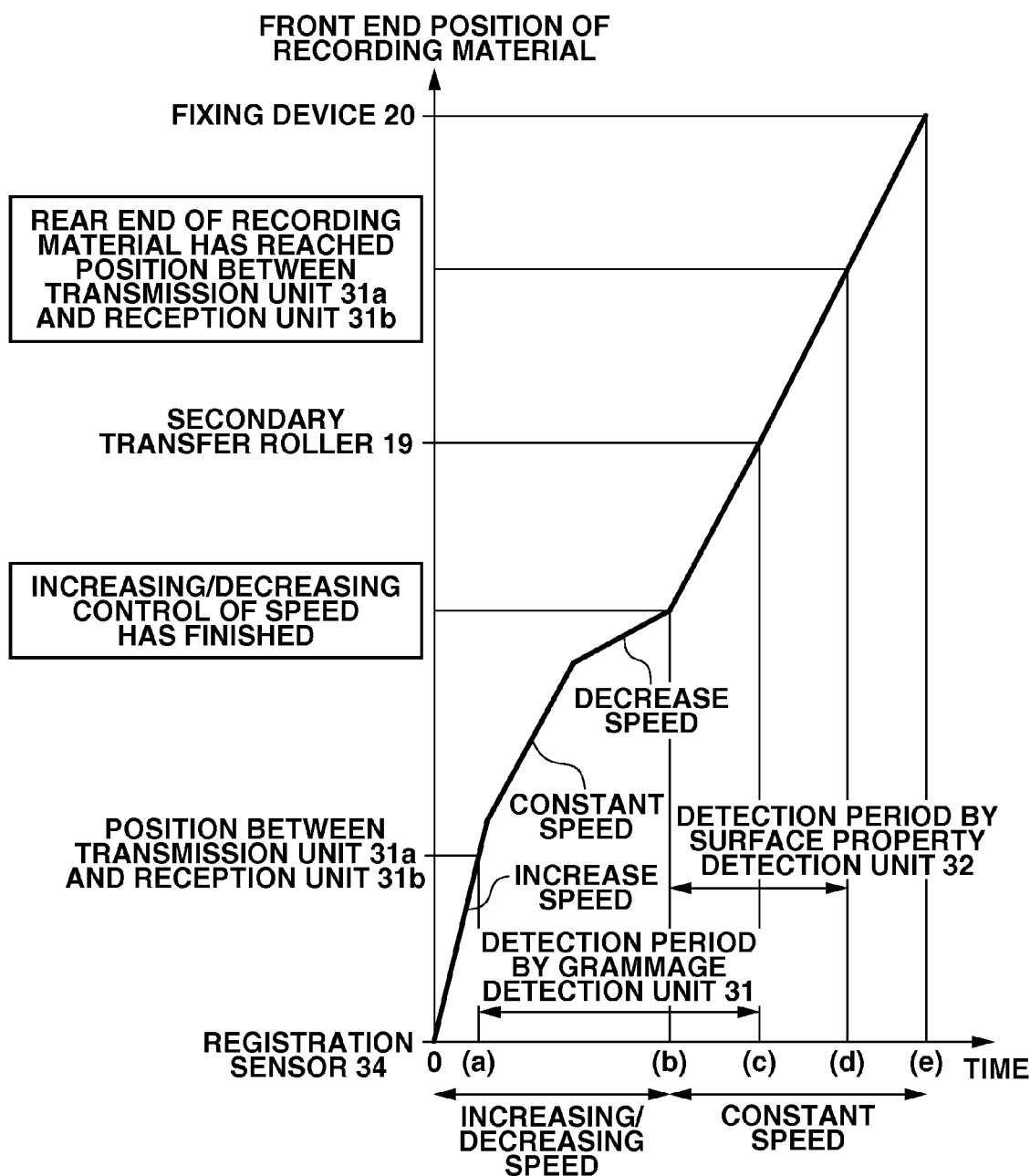
FIG. 11 is a timing chart according to the third exemplary embodiment.

The detection periods of the grammage detection unit 31 and the surface property detection unit 32 according to the present exemplary embodiment will be described with reference to a timing chart in FIG. 11. The timing chart in FIG. 11 illustrates a period from a time point at which the front end of the recording material P has passed through the sensor 34, to a time point at which the front end reaches the fixing device 20. In the present exemplary embodiment, the recording material P is conveyed while the conveyance speed of the recording material P is increased or decreased in a part of the period. A desirable detection period of the grammage detection unit 31 is, as described above, the period in which the conveyance position of the recording material P is stable, regardless of increase or decrease in the conveyance speed. This period corresponds to the period from the time point at which the front end of the recording material P has passed through the position between the transmission unit 31a and the reception unit 31b, to the time point at which the front end of the recording material P reaches the roller 19. In the timing chart in FIG. 11, the period corresponds to a period from timings (a) to (c). Herein, the timings (a) and (c) in FIG. 11 indicate the same timings as the timings (a) and (b) in FIG. 8, respectively. Accordingly, the detection period of the grammage detection unit 31 is similar to that in the second exemplary embodiment even when the conveyance speed is increased or decreased.

On the other hand, a desirable detection period of the surface property detection unit 32 is, as described above, a period in which the recording material P is conveyed at a constant speed. Therefore, in the timing chart in FIG. 11, the period corresponds to a period from timings (b) to (d) in FIG. 11. Herein, the timing (b) in FIG. 11 indicates a timing at which the increasing/decreasing control of the speed of the recording material P has finished. The timing (d) in FIG. 11 indicates the same timing as the timing (c) in FIG. 8. In FIG. 11, similarly to the second exemplary embodiment, the position between the transmission unit 31a and the reception unit 31b (detection position to be detected by the grammage detection unit 31) and the detection position to be detected by the surface property detection unit 32 are assumed to be at substantially the same position in the conveyance direction of the recording material P. Based on this assumption, the detection period of the surface property detection unit 32 is defined. The present exemplary embodiment has described the case where the length of the recording material P in the conveyance direction is shorter than the distance between the detection position detected by the surface property detection unit 32 and the fixing device 20. On the other hand, in a case where the recording material P longer in the conveyance direction than the distance is conveyed, the timing (the timing (e) in FIG. 11) at which the front end of the recording material P reaches the fixing device 20 comes earlier than the timing (the timing (d) in FIG. 11) at which the rear end of the recording material P reaches the detection position to be detected by the surface property detection unit 32. In this case, the detection period by the surface property detection unit 32 is a period from the timings (b) to (e) in FIG. 11. That is, the detection period corresponds to either one of the following periods that is shorter than the other one: the period from the time point at which the increasing/decreasing control of the speed of the recording material P has finished, to the time point at which the rear end of the recording material P reaches the detection position to be detected by the surface property detection unit 32, or the period from the time point at which the increasing/decreasing control of the speed of the recording material P has finished, to the time point at which the front end of the recording material P reaches the fixing device 20. Herein, detection by the surface property detection unit 32 is assumed to be performed for 100 ms. The detection period, however, is not limited to 100 ms. It is only required that the detection by the surface property detection unit 32 finishes in a shorter period of the above-described periods, or in a period that is further shorter than the shorter period.

A control sequence by the control unit 10 according to the present exemplary embodiment will be described with reference to a flowchart in FIG. 12. Control based on the flowchart in FIG. 12 is executed by the control unit 10 based on a program stored in a ROM (not illustrated). Control from steps S501 to S507 is performed similarly to the control in FIG. 5. After step S507, it is determined in step S701 whether 300 steps of the pulse motor have been counted. If 300 steps have been counted (YES in step S701), the control unit 10 determines that the front end of the recording material P has reached the roller 19, and then in step S702, resets the timer. In step S703, the control unit 10 instructs the start of the detection operation by the surface property detection unit 32. In step S704, it is determined whether the detection has been performed for 100 ms. If the detection has been performed for 100 ms (YES in step S704), then in step S705, the detection by the surface property detection unit 32 finishes. In step S706, the control unit 10 determines the type of recording material P based on the detection results obtained by the detection units 31 and 32, and determines image forming conditions according to the determined type. The processing then finishes.

According to the present exemplary embodiment, the above-described configuration and operation can bring about the following effects in addition to the effects obtained by the first and second exemplary embodiments. If the detection is performed in a period in which the conveyance position of the recording material P is stable, the detection accuracy of the grammage of the recording material P can be improved even when the conveyance speed of the recording material P is increased or decreased. Furthermore, improvement in the detection accuracy of grammage of the recording material P enables appropriate print mode setting, leading to enhanced quality of an image to be formed.

Furthermore, in the present exemplary embodiment, the irradiation unit 32a may irradiate the recording material P with light in the period in which the conveyance speed of the recording material P is increased or decreased. Note that, in this case, control is performed such that the result obtained through image capturing by the image capturing unit 32c is not reflected on the surface property detection result. Alternatively, the irradiation unit 32a may be controlled not to emit light in the period in which the conveyance speed of the recording material P is increased or decreased.

In the above-described exemplary embodiments, the transmission unit 31a may transmit an ultrasonic wave to the recording material P in a period in which the conveyance position of the recording material P is not stable. In this case, control is performed such that the result received by the reception unit 31b is not reflected on the grammage detection result. Alternatively, the transmission unit 31a may be controlled not to transmit the ultrasonic wave in the period in which the conveyance position of the recording material P is not stable.

In the above-described exemplary embodiments, the description has been given of the configuration in which the recording material determination unit 30 is provided with the grammage detection unit 31 and the surface property detection unit 32. The configuration, however, is not limited to this. The recording material determination unit 30 may be provided with a detection unit that irradiates the recording material P with light, receives the light transmitted through the recording material P, and detects the thickness of the recording material P based on the amount of the received light. Alternatively, the recording material determination unit 30 may be provided with, instead of the surface property detection unit 32, a detection unit that irradiates the recording material P with light, receives the light reflected on the recording material P, and detects the surface property of the recording material P based on the amount of the received light.

The above-described exemplary embodiments have described a case where a loop is formed on the recording material P between the registration roller pair 6 and the secondary transfer roller 19. The present invention is, however, not limited to this. For example, the present invention is also applicable to a configuration in which there are two conveyance units that convey the recording material P and the grammage detection unit 31 arranged therebetween, and a loop is formed between the two conveyance units.

Furthermore, the above-described exemplary embodiments have described the recording material determination unit 30 configured to be fixed to the image forming apparatus 1. The recording material determination unit 30, however, may be configured to be detachably attached to the image forming apparatus 1. When the recording material determination unit 30 is configured to be detachable, for example, a user can easily replace the recording material determination unit 30 when the unit 30 malfunctions. Alternatively, the recording material determination unit 30 may be simply configured to be additionally attachable to the image forming apparatus 1.

Figure 13A:
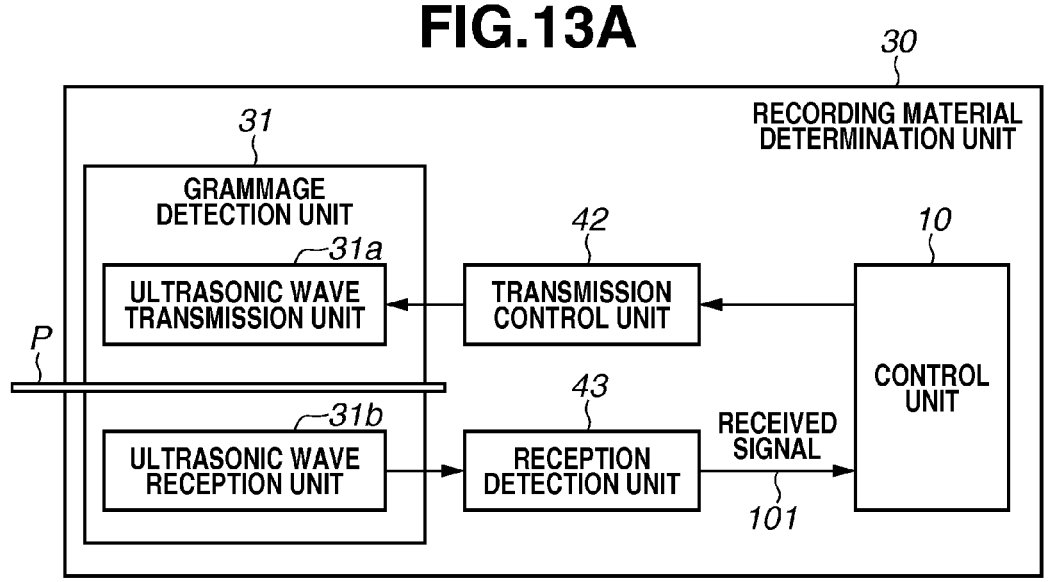
FIGS. 13A and 13B are block diagrams of a recording material determination unit according to other exemplary embodiments.
Figure 13B:
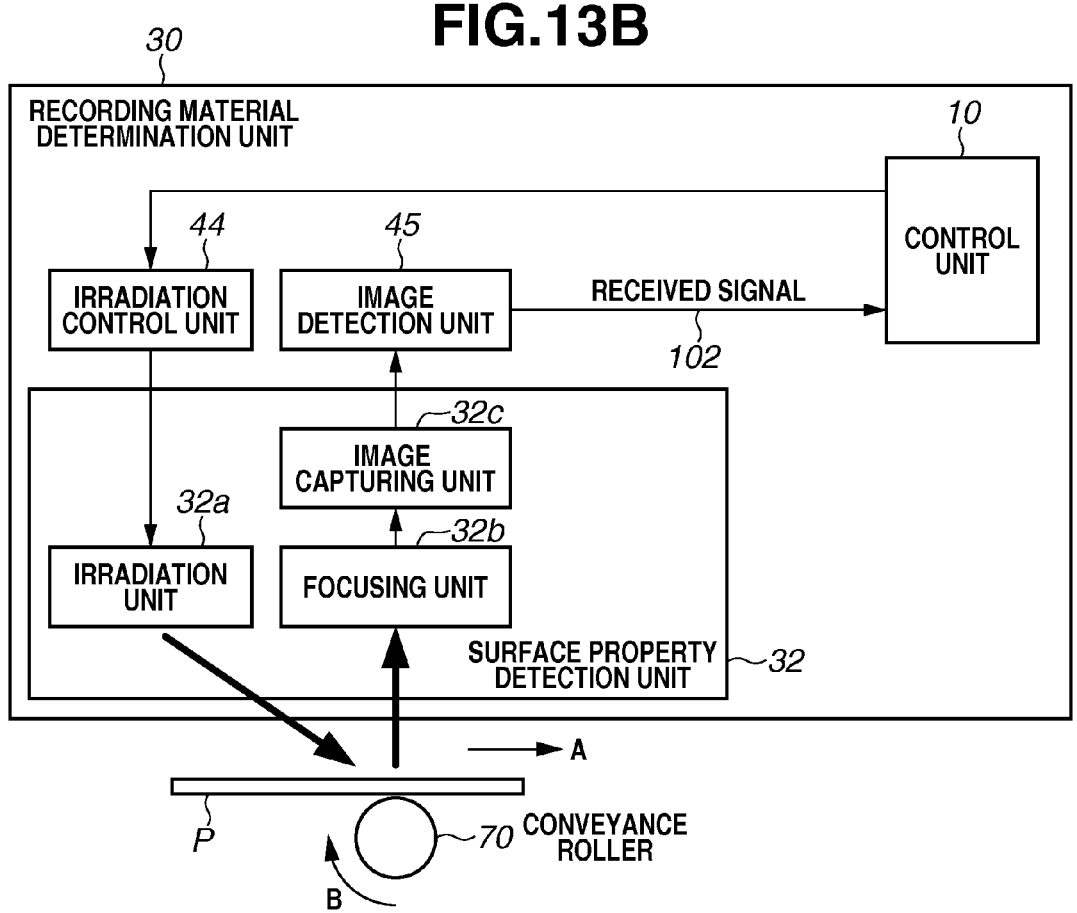

Furthermore in the above-described exemplary embodiments, the recording material determination unit 30 and the control unit 10 may be integrally formed and detachably attached to the image forming apparatus 1. This configuration is illustrated in FIGS. 13A and 13B. FIG. 13A is a block diagram of the recording material determination unit 30 including the grammage detection unit 31. FIG. 13B is a block diagram of the recording material determination unit 30 including the surface property detection unit 32. In this manner, if the recording material determination unit 30 and the control unit 10 are integrally replaceable, when updating or adding a function of the recording material determination unit 30, a user can easily replace a sensor with the one having a new function. Alternatively, the recording material determination unit 30 and the control unit 10 may be simply integrally formed, and configured to be additionally attachable to the image forming apparatus 1.

Herein, an apparatus to which the recording material determination unit 30 is attached is not limited to the image forming apparatus 1. Any conveyance apparatus may be used as long as it has a configuration for conveying the recording material P and forming a loop on the recording material P. The present invention is applicable in a state in which the recording material determination unit 30 is attached to such an apparatus.

Furthermore, although an example of a laser beam printer has been described in the above-described exemplary embodiments, the image forming apparatus to which the present invention is applied is not limited to the laser beam printer. The image forming apparatus may be a printer with other printing methods such as an inkjet printer, or may be a copier.

Hereinafter, fourth to sixth exemplary embodiments of the present invention will be described with reference to the drawings. The following exemplary embodiments are only examples. The present invention is not limited to the exemplary embodiments described herein. In the following drawings, components that are not necessary for describing the exemplary embodiments will be omitted.

FIG. 14 is a configuration diagram of an image forming apparatus according to a fourth exemplary embodiment. The same components as those illustrated in FIG. 1 are assigned the same reference signs. Last letters Y, M, C, and K of reference signs indicate that corresponding members are members for forming developer images of the respective colors of yellow (Y), magenta (M), cyan C, and black (K). When it is not necessary to distinguish colors, the reference signs without the last letters Y, M, C, and K are used herein. Photosensitive drums 11 serve as an image bearing member, and are driven to rotate during image formation. Charging units (rollers) 12 charge the surfaces of the respective photosensitive drums 11 to a uniform potential. Exposure units 13 scan and expose the surfaces of the respective photosensitive drums 11 with light according to image data of images to be formed, to thereby form electrostatic latent images on the photosensitive drum 11. Development units 14 contain developers of the respective colors. The development units 14 develop the electrostatic latent images on the respective photosensitive drums 11 by supplying the developers to the electrostatic latent images on the photosensitive drums 11 using the respective developing rollers 15. Primary transfer rollers 16 output a primary transfer bias, and transfer the developer images formed on the photosensitive drums 11, onto the intermediate transfer belt 17, which is an image bearing member and is stretched by rollers 180, 200 and 250. At this time, a color image is formed by transferring the developer images on the respective photosensitive drums 11, onto the intermediate transfer belt 17 in a superimposed manner.

The developer image formed on the intermediate transfer belt 17 is conveyed to a counter position of the secondary transfer roller 19 by rotation of the intermediate transfer belt 17. A sheet feeding roller 4 feeds the recording material P stored in the cassette 2 to a conveyance path. A conveyance roller 63 and a conveyance counter roller 60 constitute a roller pair for conveying the recording material P. When a registration sensor 340 detects the recording material P, the conveyance roller 63 and the conveyance counter roller 60 temporarily stop conveying the recording material P. The conveyance roller 63 and the conveyance counter roller 60 restart conveying the recording material P, according to the timing at which the developer image formed on the intermediate transfer belt 17 comes to the counter position of the secondary transfer roller 19. The secondary transfer roller 19 outputs a secondary transfer bias, thereby transferring the developer image on the intermediate transfer belt 17, onto the recording material P. The secondary transfer roller 19 is also involved in conveyance of the recording material P. That is, the secondary transfer roller 19 is a member that acts on the recording material P for transferring the developer image onto the recording material P and is a member for conveying the recording material P. Then, at a fixing unit 210, heat and pressure are applied to the recording material P on which the developer image has been transferred, whereby the developer image is fixed onto the recording material P. The recording material P on which the developer image has been fixed is output to a discharge tray 260 by a discharge roller 220.

In the present exemplary embodiment, grammage of the recording material P is detected as a characteristic of the recording material P. As illustrated in FIG. 14, a grammage detection sensor that detects the grammage of the recording material P is provided on an upstream side of the secondary transfer roller 19 in a conveyance direction of the recording material P. The grammage detection sensor includes a transmission unit 310 and a reception unit 320. The transmission unit 310 is arranged opposite the reception unit 320 across the conveyance path. Furthermore, a guide roller 330 is arranged on the same side of the transmission unit 310. The guide roller 330 is a member for stabilizing conveyance position of the recording material P by absorbing vibration during conveyance of the recording material P. The guide roller 330 is an example of a contact member that contacts the recording material P. The transmission unit 310 and the guide roller 330 together with the secondary transfer roller 19 are held by a secondary transfer unit 230. The secondary transfer unit 230 is openable and closable in the direction indicated by an arrow in FIG. 14, around a rotation shaft 240 as a fulcrum. With this configuration, when the recording material P being conveyed is jammed near the secondary transfer unit 230, the user can easily remove the jammed recording material P. The grammage is a mass of a recording material P per unit area, and the unit is $[g/m^2]$.

The transmission unit 310 and the reception unit 320 have a similar configuration. Each of the units 310 and 320 includes a piezoelectric element, which is a mutual conversion element for mechanical displacement and an electric signal, and an electrode terminal. In the transmission unit 310, when a pulse voltage with a predetermined frequency is input to the electrode terminal, the piezoelectric element oscillates to generate an ultrasonic wave, which is propagated in the air. When the ultrasonic wave reaches the recording material P, the ultrasonic wave vibrates the recording material P. In this manner, the ultrasonic wave generated by the transmission unit 310 is propagated to the reception unit 320 through the recording material P. The piezoelectric element of the reception unit 320 generates on the electrode terminal the output voltage according to the amplitude of the received ultrasonic wave. This is an operation principle of a case where the ultrasonic wave is transmitted and received using the piezoelectric element.

Vibration of the conveyance roller 63 is transmitted to the recording material P being conveyed. This flapping caused by the vibration during conveyance affects the detection result of grammage. The reason is as follows. A tilt in the recording material P with respect to the ultrasonic wave path changes the area of the recording material P that is in contact with the ultrasonic wave, causing a fluctuation in the ultrasonic wave to be propagated to the reception unit 320. The image forming apparatus according to the present exemplary embodiment performs the detection of grammage a plurality of times to suppress the above-described influence. For increasing the number of detections of grammage, the image forming apparatus detects grammage even after the recording material P has reached the counter position of the secondary transfer roller 19. Herein, if the rotation speed of the conveyance roller 63 is higher than that of the secondary transfer roller 19, the recording material P is pulled in the conveyance direction to generate a bending (loop) of the recording material P.

Figure 15A:
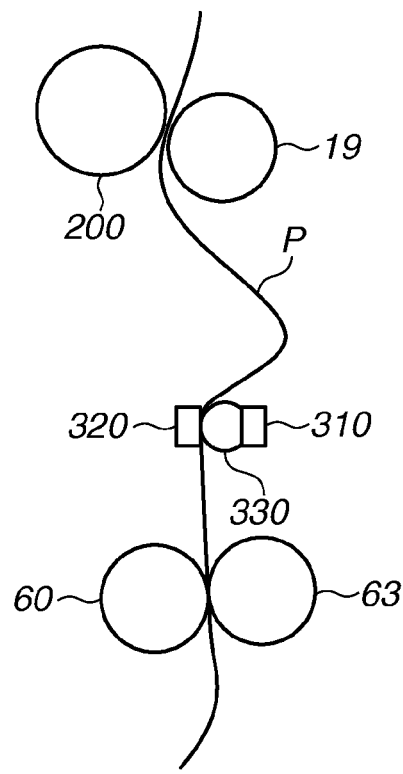
FIGS. 15A to 15D are diagrams for describing erroneous determination due to bending in the recording material.
Figure 15B:
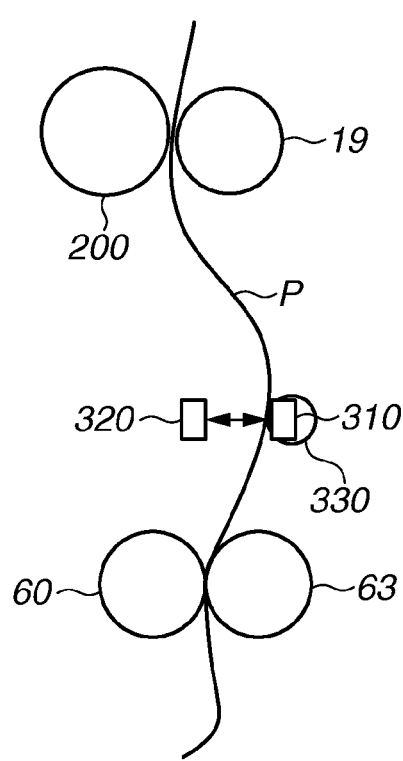
Figure 15C:
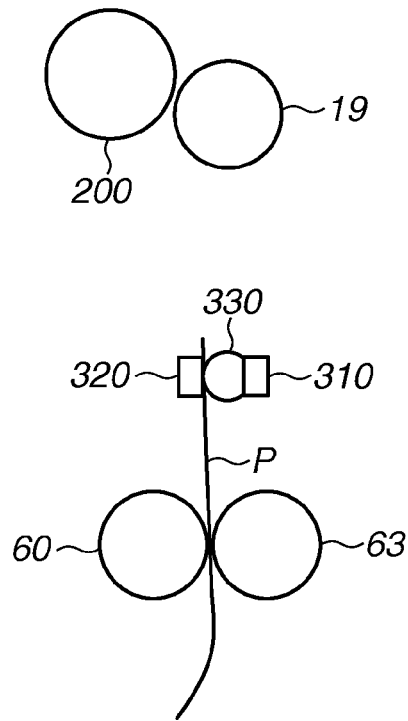
Figure 15D:
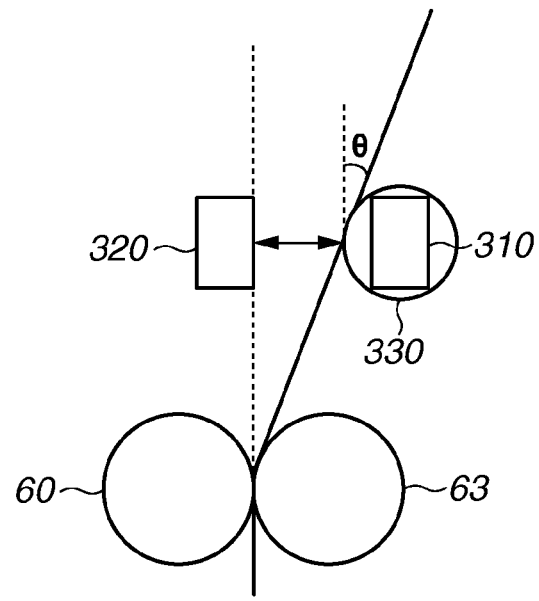
Figure 23A:
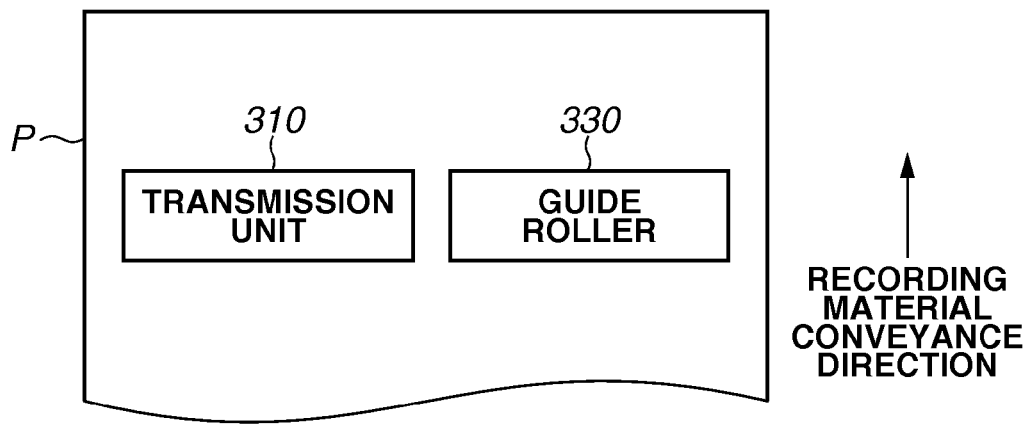
FIGS. 23A to 23C are diagrams illustrating positional relationships between a grammage detection sensor and a guide roller of the image forming apparatus, and the recording material according to the fourth exemplary embodiment.
Figure 23B:
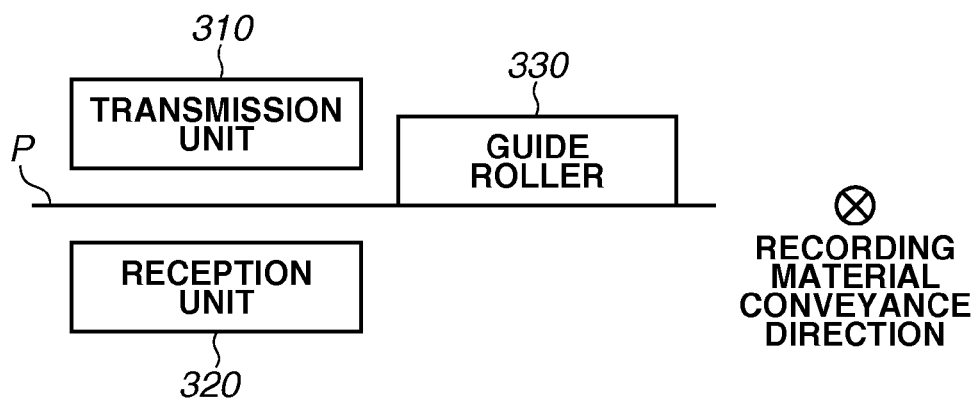
Figure 23C:
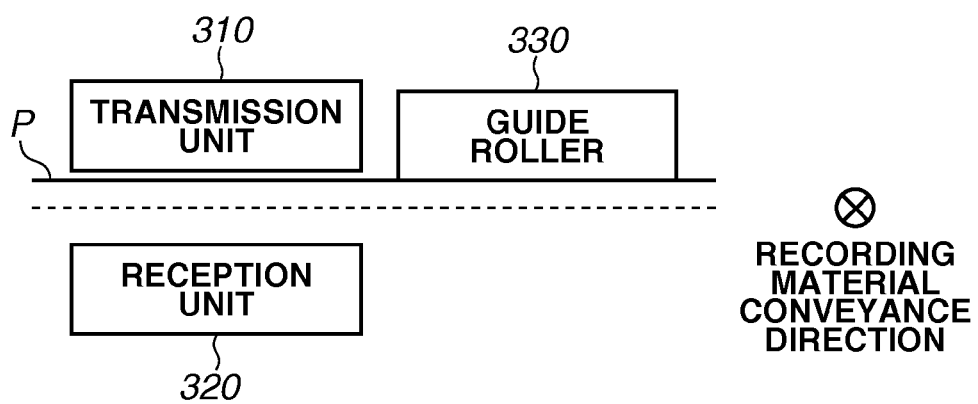

Reasons for occurrence of bending and for occurrence of an error in the detection result of grammage due to the bending will be described with reference to FIGS. 15A to 15D and FIGS. 23A to 23C. In the case of FIG. 15A, in which the recording material P is thin paper, even if bending of the recording material P occurs, the bending on the sensor can be suppressed by the guide roller 330. On the other hand, in the case of FIG. 15B, in which the recording material P is thick paper, repulsion of the recording material P increases and the bending cannot be suppressed by the guide roller 330. This causes the bending that may lift up the guide roller 330. In this case, as illustrated in FIG. 15D, a tilt θ occurs in the recording material P between the transmission unit 310 and the reception unit 320. Accordingly, the obtained grammage differs from that in the detection result of FIG. 15C, in which no tilt occurs in the recording material P. A rotation speed difference between the conveyance roller 63 and the secondary transfer roller 19 is caused by the use of different driving sources. Nevertheless, even when the same driving source is used, the rotation speed difference may be caused by another factor such as the difference in slippage between the roller and the recording material P. FIG. 23A illustrates the positional relationship between the grammage detection sensor and the guide roller 330 viewed in a direction orthogonal to the surface of the recording material P. As illustrated in FIGS. 15A to 15D, the transmission unit 310 of the grammage detection sensor and the guide roller 330 are provided on the same side with respect to the recording material P. On the opposite side to the transmission unit 310 with respect to the recording material P, the reception unit 320 is provided, which is not illustrated in FIG. 23A. FIGS. 23B and 23C are diagrams viewed in the conveyance direction of the recording material P. Herein, FIG. 23B illustrates the state in which no bending occurs in the recording material P. FIG. 23C illustrates the state in which bending has occurred in the recording material P. The dotted line in FIG. 23C indicates the position of the recording material P when no bending occurs.

Figure 16:
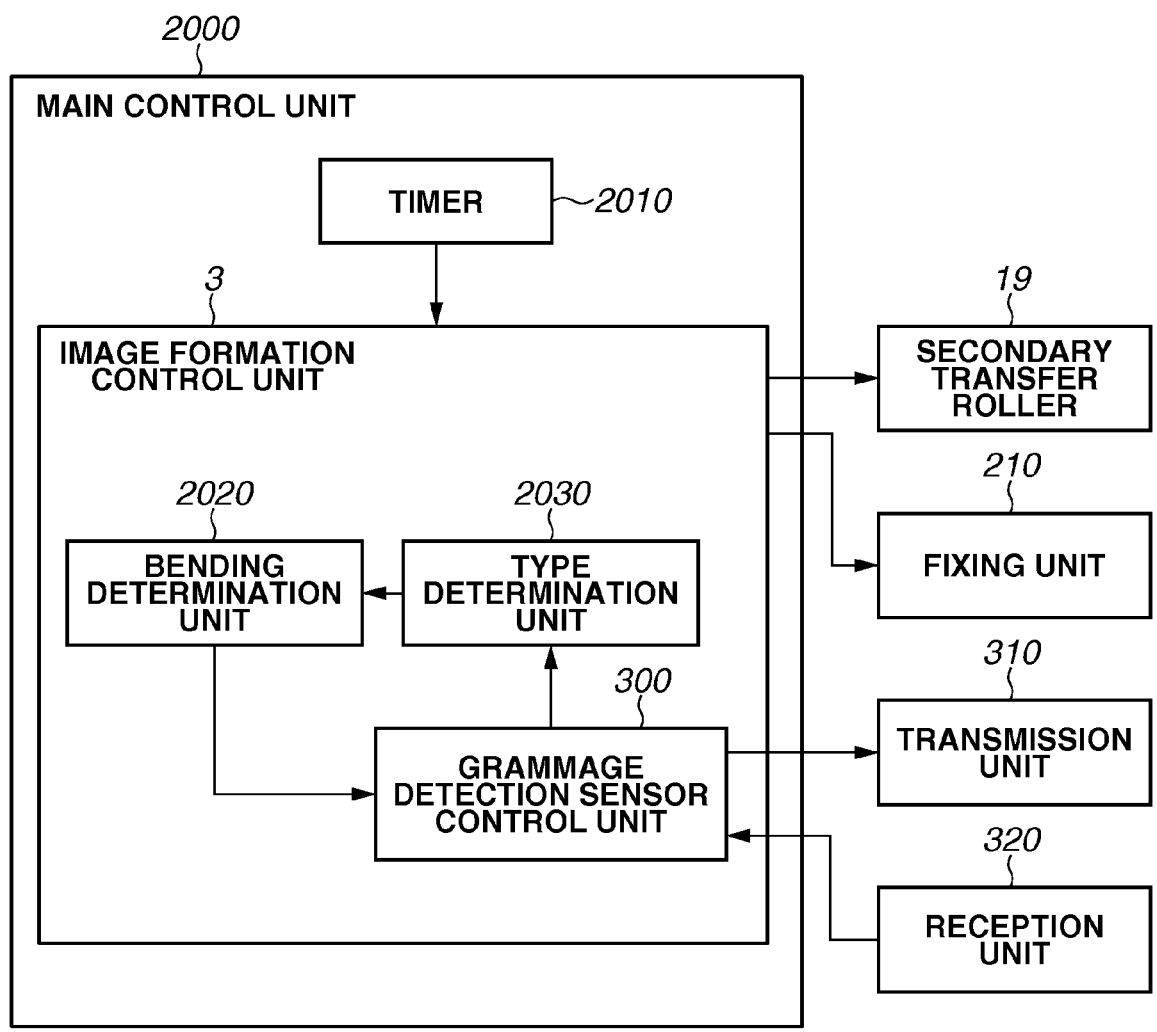
FIG. 16 is a diagram illustrating a control configuration of the image forming apparatus according to the fourth exemplary embodiment.

FIG. 16 is a functional block diagram illustrating a control configuration of the image forming apparatus according to the present exemplary embodiment. A main control unit 2000 controls the entire image forming apparatus, and includes a timer 2010 and an image formation control unit 3. How the timer 2010 is utilized will be described below. The image formation control unit 3 includes a grammage detection sensor control unit 300 that controls the grammage detection sensor. The grammage detection sensor control unit 300 transmits an ultrasonic wave generation instruction to the transmission unit 310 and receives a result from the reception unit 320. A type determination unit 2030 determines grammage based on the detection result obtained by the grammage detection sensor control unit 300. Furthermore, the type determination unit 2030 determines, based on the determined grammage, the type of recording material P and sets image forming conditions. Herein, the image forming conditions are conditions of which values are changed depending on the type of recording material P. For example, the image forming conditions include the conveyance speed of the recording material P, the voltage to be applied to the secondary transfer roller 19, and a fixing temperature of the fixing unit 210. A bending determination unit 2020 determines, based on the type of recording material P that has been determined by the type determination unit 2030, whether bending occurs, and notifies the grammage detection sensor control unit 300 of the determination result. The grammage detection sensor control unit 300 controls the timing for performing the grammage detection, based on the determination result obtained by the bending determination unit 2020.

Figure 17:
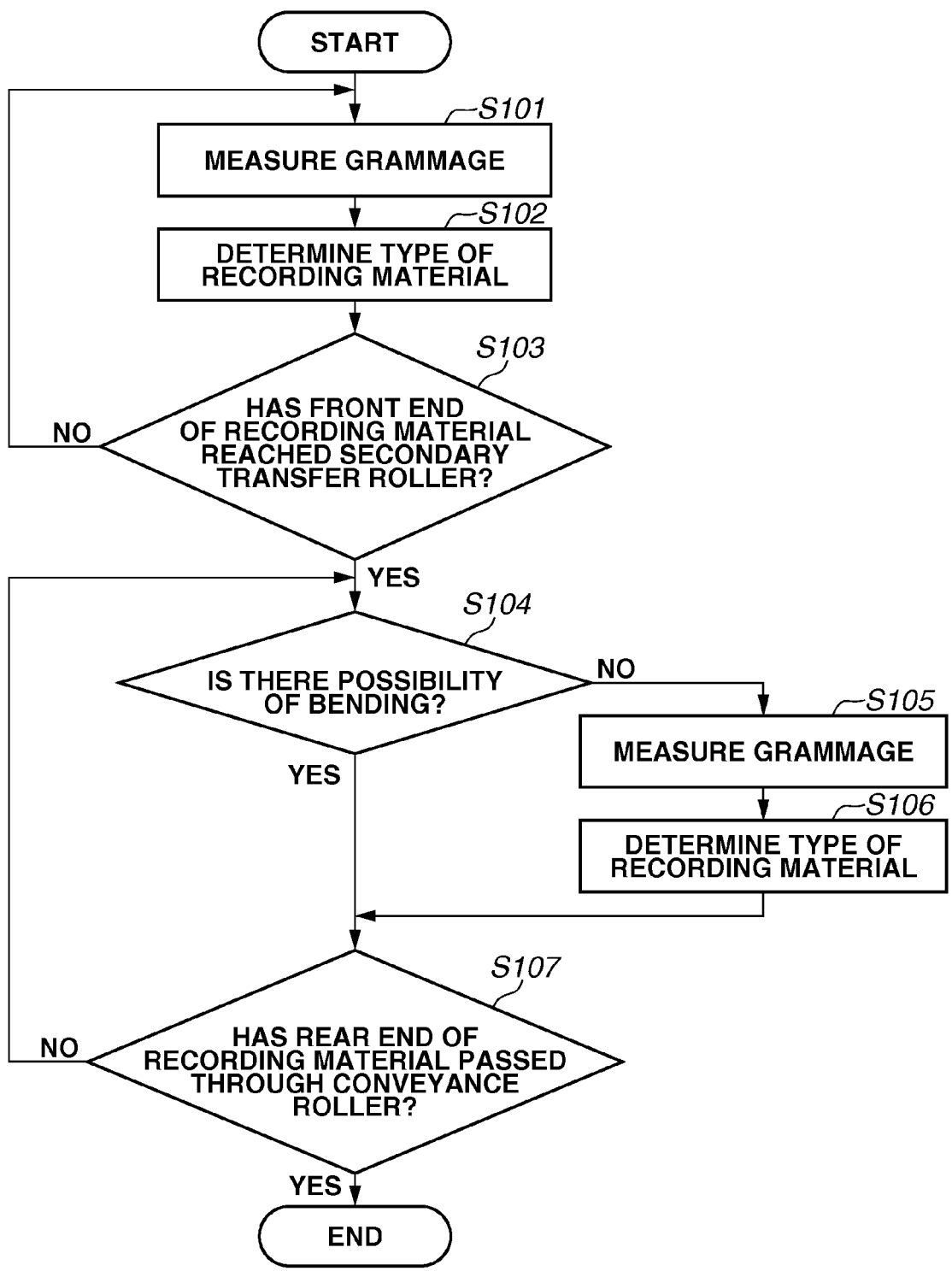
FIG. 17 is a flowchart illustrating type determination processing of the recording material according to the fourth exemplary embodiment.

FIG. 17 is a flowchart illustrating type determination processing of the recording material P. In step S101, the grammage detection sensor control unit 300 measures the grammage of the recording material P using the grammage detection sensor. As illustrated in FIG. 15C, the process in step S101 is performed in a state in which the recording material P is in a position where it is detectable by the grammage detection sensor, but it has not reached the secondary transfer roller 19. In step S102, the type determination unit 2030 determines the type of recording material P based on the measurement result obtained in step S101. In step S103, the image formation control unit 3 determines whether the front end of the recording material P has reached the secondary transfer roller 19, and if not (No in step S103), the processing is repeated from step S101. The type determination unit 2030 can be configured to determine the type of recording material based on a plurality of measurement results of grammage, in repetition of steps S101 to S103. The bending determination unit 2020 determines, every time the type determination unit 2030 determines the type, whether the determined type is the type that lifts up the guide roller 330, namely, the type that generates bending, and notifies the grammage detection sensor control unit 300 of the determination result. If the front end of the recording material P has reached the secondary transfer roller 19 (YES in step S103), then in step S104, the grammage detection sensor control unit 300 determines whether the determination result obtained by the bending determination unit 2020 indicates that bending occurs. When the recording material is determined to be not the type that bends (NO in step S104), then in step S105, the grammage detection sensor control unit 300 measures the grammage of the recording material P by the grammage detection sensor. In step S106, the type determination unit 2030 determines the type of recording material P. The type determination unit 2030 may be configured to determine the type of recording material P based on a plurality of previous measurement results of grammage. In step S107, the grammage detection sensor control unit 300 determines whether the rear end of the recording material P has passed through the conveyance roller 63, and if the rear end has not passed (NO in step S107), the processing is repeated from step S104 until the rear end passes through the roller 63. On the other hand, if it is determined in step S104 that the determination result obtained by the bending determination unit 2020 indicates that the type of the recording material P is the type that generates bending (YES in step S104), the grammage detection sensor control unit 300 discontinues grammage measurement by the grammage detection sensor after the front end of the recording material P has reached the secondary transfer roller 19. The image formation control unit 3 determines the time when the recording material P reaches the counter position of the secondary transfer roller 19, based on the time measured by the timer 2010 in FIG. 16.

In this manner, whether bending occurs is determined based on the type of recording material P that has been determined in a state in which the recording material P has not reached the counter position of the secondary transfer roller 19. If it is determined that bending may occur, type determination for the recording material P is stopped after the recording material P has reached the counter position of the secondary transfer roller 19. This can prevent erroneous detection caused by performing type determination in a state in which bending has occurred.

In the present exemplary embodiment, the type determination unit 2030 determines, based on the grammage of the recording material P, the type of recording material P. According to the determination result, the bending determination unit 2020 determines whether the recording material P lifts up the guide roller 330. Herein, information related to the grammage of the recording material P includes information on the thickness of the recording material P. If the recording material P is made of the same material, the larger the thickness of the recording material P, the larger the grammage of the recording material P. The information on the thickness of the recording material P can be obtained, for example, by emitting light onto the recording material P and receiving the transmitted light transmitted through the recording material P. In this case, for example, the transmission unit 310 and the reception unit 320 in FIG. 14 are respectively replaced with a light emitting unit and a light receiving unit. At this time, the light receiving unit that receives transmitted light may be a photodiode, or may be an area sensor or a line sensor that captures the received light as an image. The line sensor is a sensor extending in a direction orthogonal to the conveyance direction of the recording material P, and can capture an image while conveying the recording material P.

When the amount of light received by the light receiving unit is large, the type determination unit 2030 determines that the thickness of the recording material P is thin, and then determines that the type of recording material P is thin paper. When the amount of the received light is small, the type determination unit 2030 determines that the thickness of the recording material P is thick, and then determines that the type of recording material P is thick paper. In this manner, by using the thickness detection sensor that detects the thickness of the recording material P, the type of recording material P can be determined similarly to the case where the grammage detection sensor according to the present exemplary embodiment is used. Furthermore, if thick paper with high stiffness lifts up the guide roller 330 and a tilt occurs in the recording material P as illustrated in FIG. 15D, the amount of light transmitted through the recording material P changes. Therefore, obtained thickness information differs from the detection result obtained in a state in which no tilt occurs in the recording material P as in FIG. 15C.

In this manner, whether bending occurs is determined based on the type of recording material P determined by the thickness detection sensor in a state in which the recording material P has not reached the counter position of the secondary transfer roller 19, in a similar manner to the case of using the grammage detection sensor. Subsequently, if it is determined that bending may occur, type determination for the recording material P using the thickness detection sensor may be stopped after the recording material P has reached the counter position of the secondary transfer roller 19.

Figure 18:
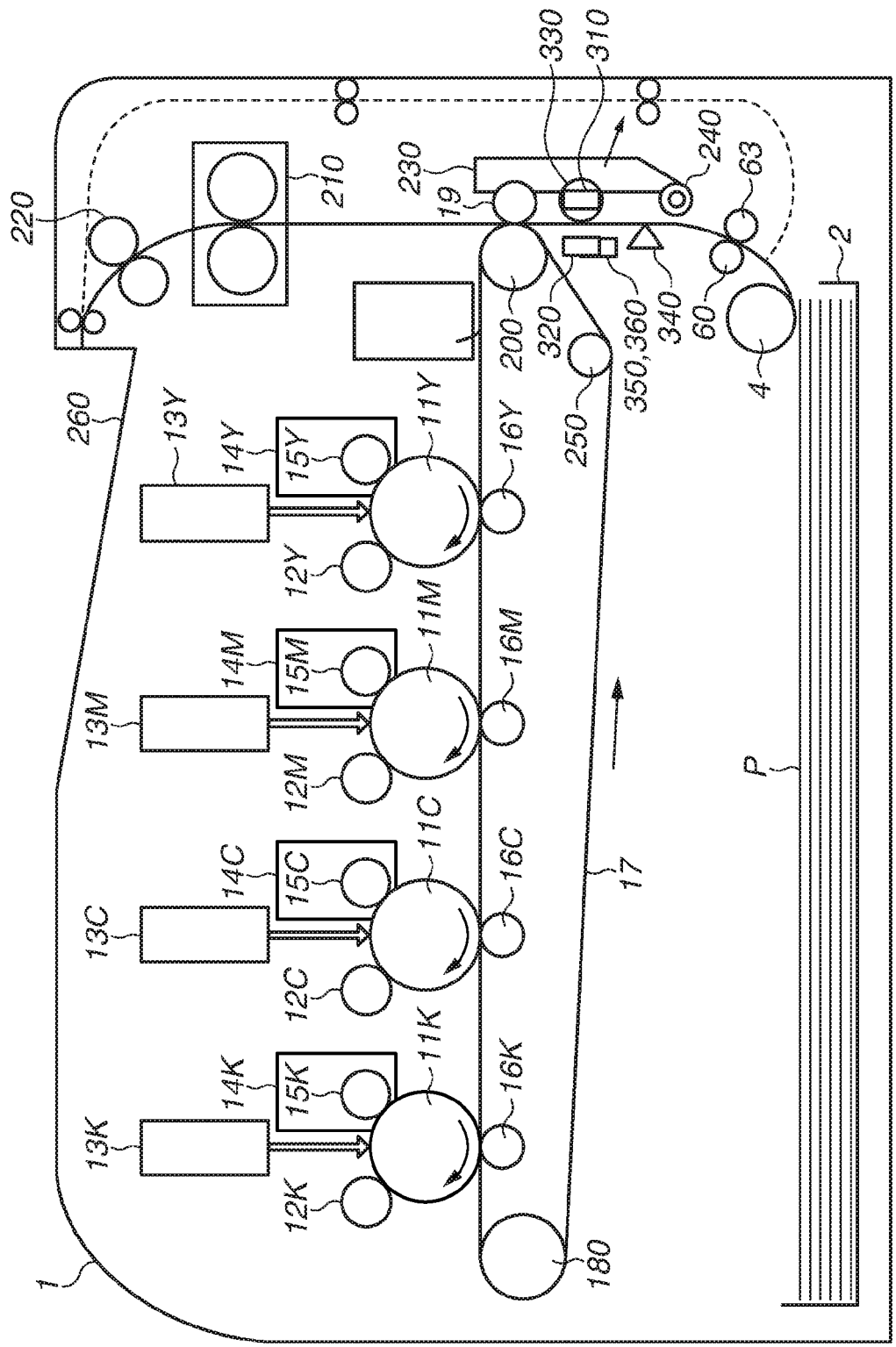
FIG. 18 is a configuration diagram of an image forming apparatus according to a fifth or sixth exemplary embodiment.
Figure 24A:
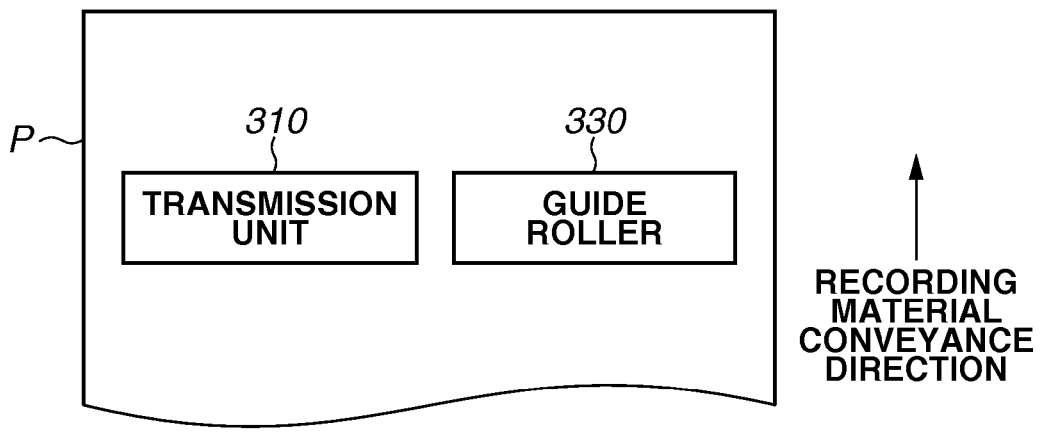
FIGS. 24A to 24C are diagrams illustrating positional relationships between a grammage detection sensor, a surface property detection sensor, and a guide roller of the image forming apparatus, and the recording material according to the fifth or sixth exemplary embodiment.
Figure 24B:
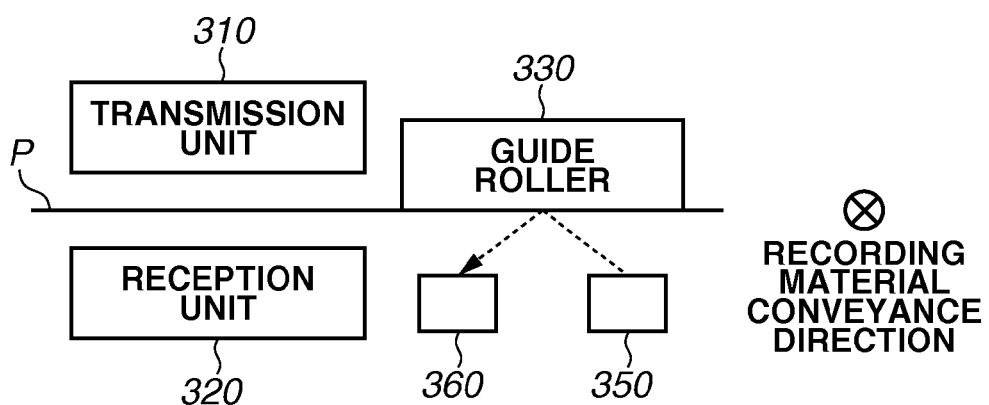
Figure 24C:
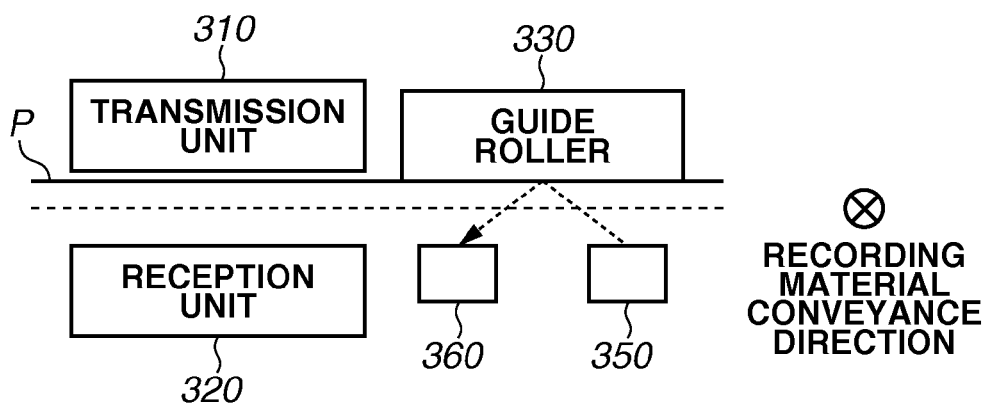

Next, a fifth exemplary embodiment will be described mainly on a difference from the fourth exemplary embodiment. FIG. 18 is a configuration diagram of an image forming apparatus according to the present exemplary embodiment. The image forming apparatus according to the present exemplary embodiment differs from the image forming apparatus according to the fourth exemplary embodiment in that a surface property detection sensor is added. The surface property detection sensor for detecting the surface information of the recording material P, as one characteristic of the recording material P, includes a light emitting element 350 and a light receiving element 360 (photodiode) as a light receiving unit that receives light. The guide roller 330 is arranged at a position facing the surface property detection sensor. The transmission unit 310 and the guide roller 330 together with the secondary transfer roller 19 are held by the secondary transfer unit 230. In the present exemplary embodiment, the light receiving element 360 receives the light emitted from the light emitting element 350 and reflected on the recording material P as reflected light. As illustrated in FIG. 18, the light receiving element 360 and the light emitting element 350 are provided on the same side with respect to the recording material P. FIGS. 24A to 24C illustrate the positional relationship between the grammage detection sensor, the surface property detection sensor, the guide roller 330, and the recording material P. As illustrated in FIG. 24A, the transmission unit 310 of the grammage detection sensor and the guide roller 330 are provided on the same side with respect to the recording material P. On the opposite side to the transmission unit 310 and the guide roller 330 with respect to the recording material P, there are provided the reception unit 320 of the grammage detection sensor and the light emitting element 350 and the light receiving element 360 of the surface property detection sensor, although they are not illustrated in FIG. 24A. FIGS. 24B and 24C are diagrams viewed in the conveyance direction of the recording material P. Herein, FIG. 24B illustrates a state in which no bending occurs in the recording material P. FIG. 24C illustrates a state in which bending has occurred in the recording material P. In FIGS. 24B and 24C, the dotted arrows indicate light emitted from the light emitting element 350, reflected on the recording material P, and then received by the light receiving element 360. The dotted line in FIG. 24C indicates the position of the recording material P when no bending occurs. The light receiving unit may be an area sensor or a line sensor that captures the received light as an image.

Figure 19:
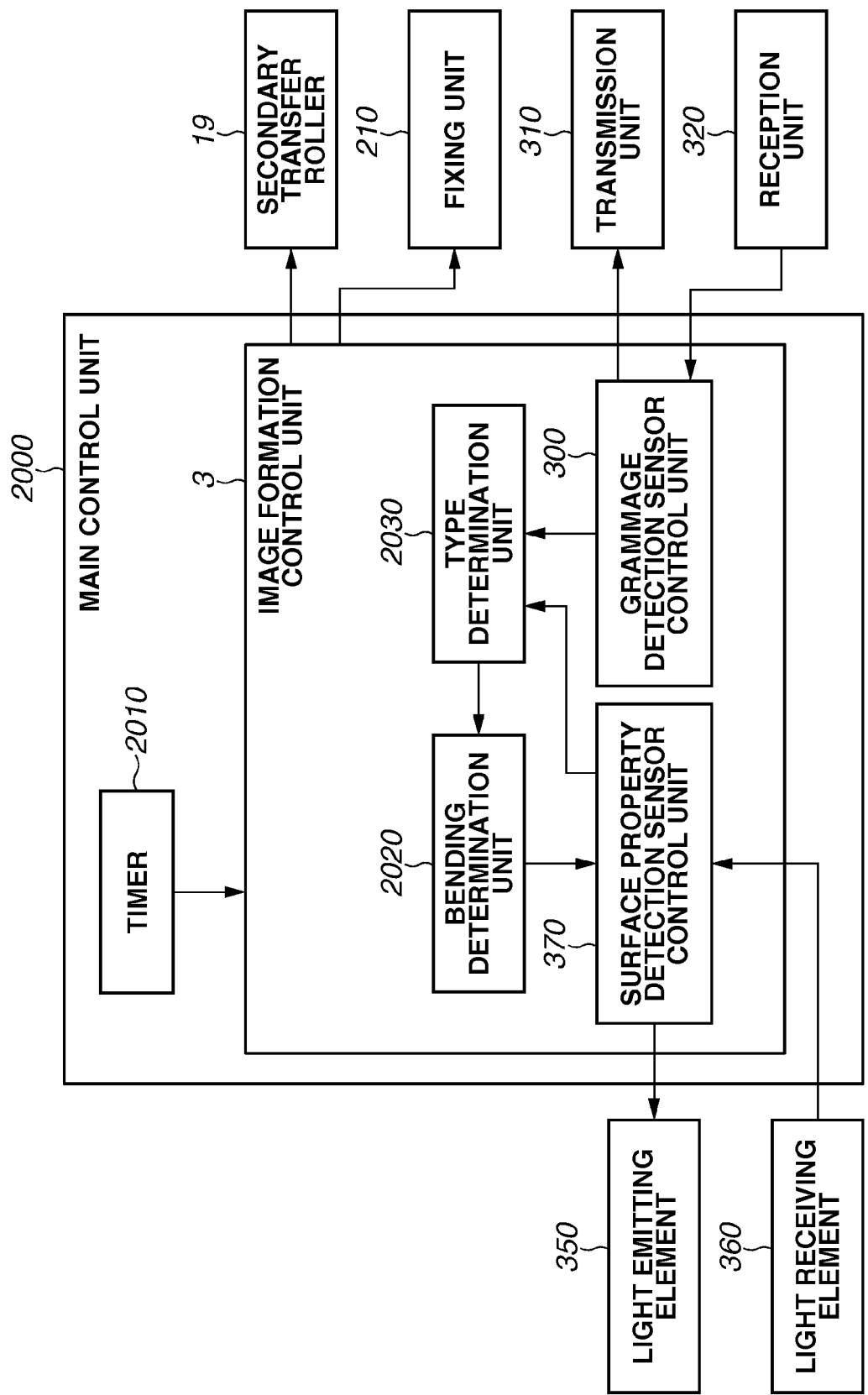
FIG. 19 is a diagram illustrating a control configuration of the image forming apparatus according to the fifth exemplary embodiment.

FIG. 19 is a functional block diagram illustrating a control configuration of the image forming apparatus according to the present exemplary embodiment. A surface property detection sensor control unit 370 controls light emission of the light emitting element 350 and obtains the amount of light received by the light receiving element 360. In the present exemplary embodiment, the type determination unit 2030 determines the type of recording material P based on the detection result obtained by the grammage detection sensor control unit 300 or the surface property detection sensor control unit 370, and controls image forming conditions. In the present exemplary embodiment, the type of recording material P is determined based on the grammage until the front end of the recording material P reaches the counter position of the secondary transfer roller 19. On the other hand, after the front end of the recording material P has reached the counter position of the secondary transfer roller 19, the type of recording material P is determined based on the surface property if the recording material P is the one that does not bend.

Figure 20:
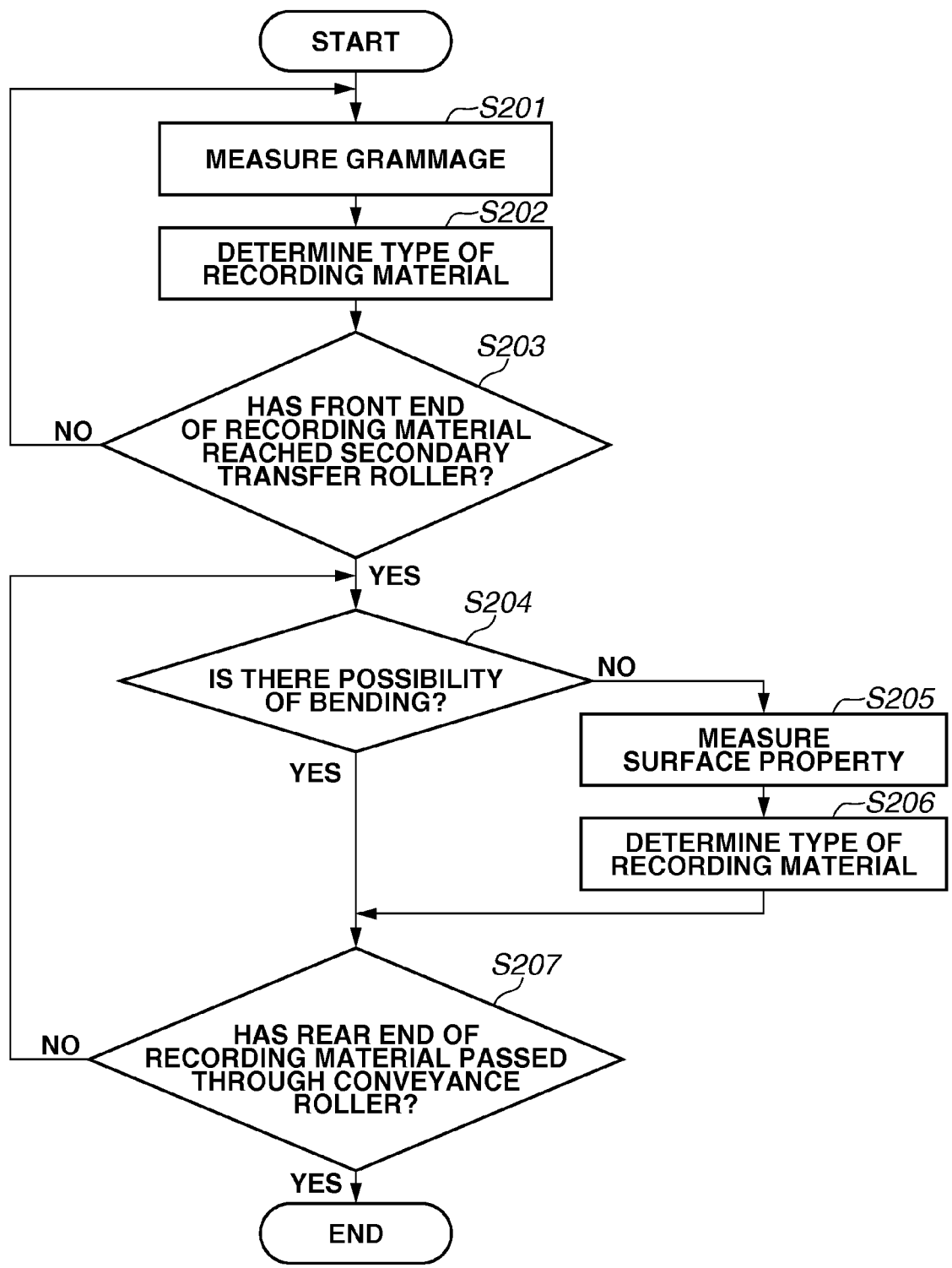
FIG. 20 is a flowchart illustrating type determination processing of the recording material according to the fifth exemplary embodiment.

FIG. 20 is a flowchart illustrating type determination processing of the recording material P. Processing in steps S201 to S204 and the processing in S207 are the same as the processing in steps S101 to S104 and the processing in step S107 in FIG. 17. In the present exemplary embodiment, after the front end of the recording material P has reached the counter position of the secondary transfer roller 19, if the recording material P is not the one that may bend, the type of recording material P is determined based on the surface property. Specifically, in step S205, the surface property detection sensor control unit 370 measures the surface proper of the recording material P by the surface property detection sensor. In step S206, the type determination unit 2030 determines the type of recording material P based on the surface property of the recording material P.

In the present exemplary embodiment, type determination in step S202 is performed based on the grammage. The type determination, however, may be performed based on the grammage in combination with the surface property. Furthermore, in the present exemplary embodiment, the type determination in step S206 is performed based on the surface property. The type determination, however, may be performed based on the surface property in combination with the grammage, or only based on the grammage.

Furthermore, as described in the fourth exemplary embodiment, a sensor that detects the thickness may be used instead of a sensor that detects grammage. That is, while the type determination in step S202 is performed based on the grammage in the present exemplary embodiment, the type determination may be performed based on the thickness. Alternatively, the type determination may be performed based on the thickness in combination with the surface property. Furthermore, in the present exemplary embodiment, the type determination in step S206 is performed based on the surface property. The type determination, however, may be performed based on the thickness in combination with the surface property, or only based on the thickness.

Next, a sixth exemplary embodiment will be described mainly on a difference from the fifth exemplary embodiment. In the present exemplary embodiment, the occurrence of bending is determined by comparing the detection results obtained by the surface property detection sensor between before and after the front end of the recording material P has reached the counter position of the secondary transfer roller 19.

Figure 21:
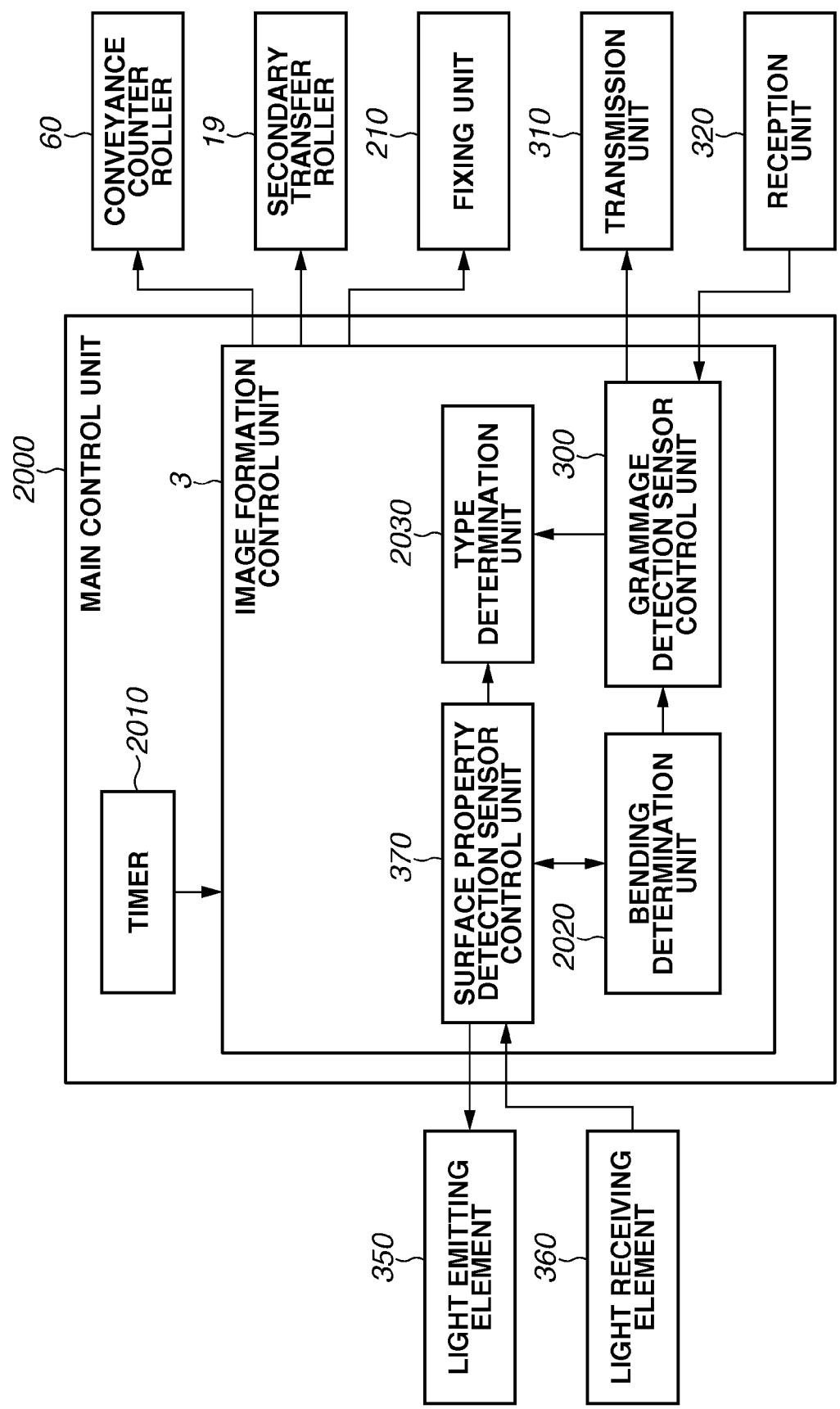
FIG. 21 is a diagram illustrating a control configuration of the image forming apparatus according to the sixth exemplary embodiment.

FIG. 21 is a functional block diagram illustrating a control configuration of an image forming apparatus according to the present exemplary embodiment. As described above, the bending determination unit 2020 determines the occurrence of bending based on the detection results obtained by the surface property detection sensor before and after the front end of the recording material P has reached the counter position of the secondary transfer roller 19, and notifies the grammage detection sensor control unit 300 of the determination result. Specifically, when bending occurs, the amount of light received by the light receiving element 360 of the surface property detection sensor decreases as compared with that in the case where no bending occurs. Accordingly, the bending determination unit 2020 determines that bending has occurred, when the amount of light received by the light receiving element 360 after the front end of the recording material P has reached the counter position of the secondary transfer roller 19 decreases by a predetermined threshold or more from that obtained before the front end reaches the counter position.

Figure 22:
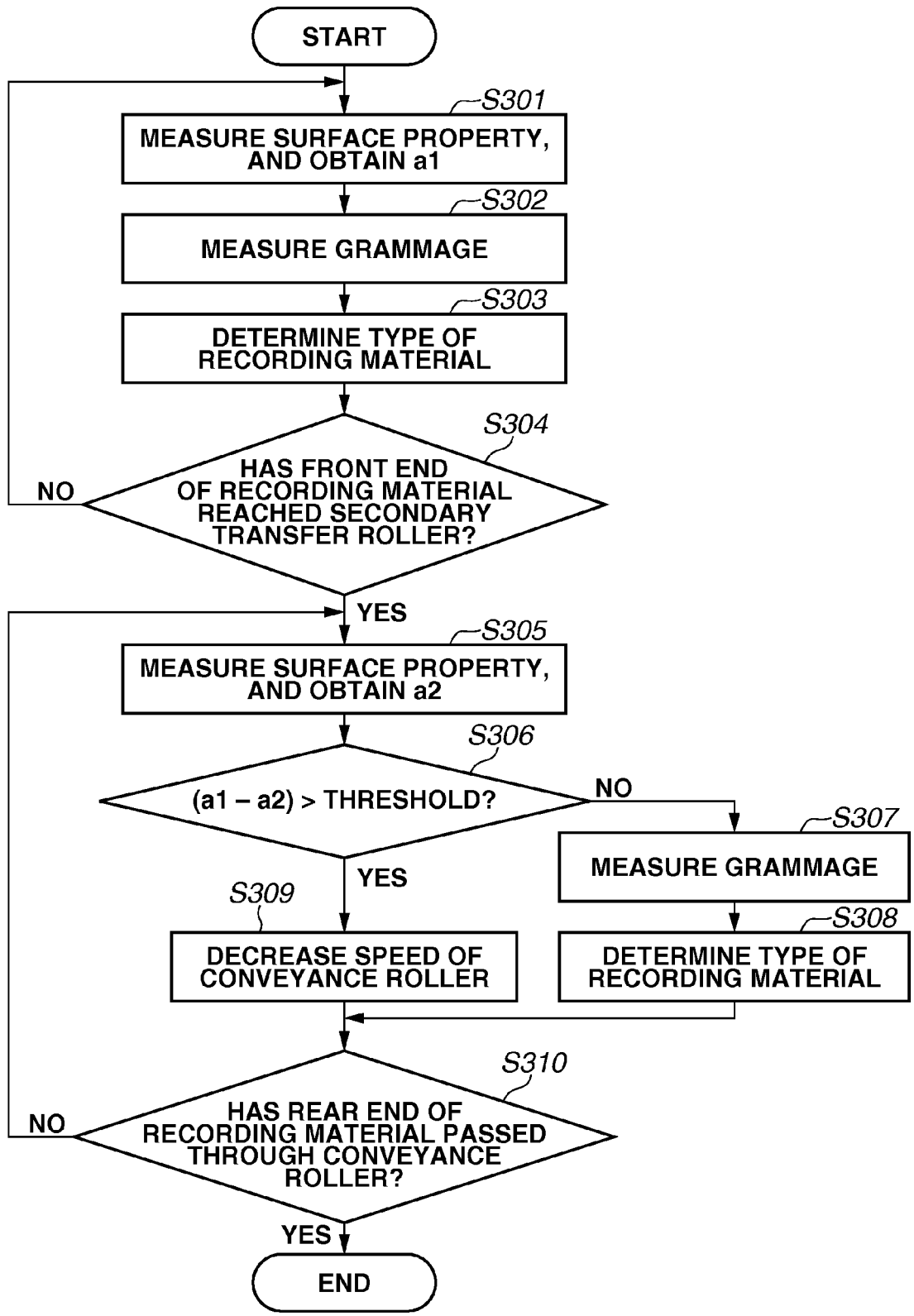
FIG. 22 is a flowchart illustrating type determination processing of the recording material according to the sixth exemplary embodiment.

FIG. 22 is a flowchart illustrating type determination processing of the recording material P. In step S301, the surface property detection sensor control unit 370 measures the surface property of the recording material P by the surface property detection sensor. The amount of light received by the light receiving element 360 at this time is defined as a1. In step S302, the grammage detection sensor control unit 300 measures the grammage of the recording material P by the grammage detection sensor. In step S303, the type determination unit 2030 determines the type of recording material P based on the grammage. In step S304, it is determined whether the front end of the recording material P has reached the secondary transfer roller 19. If it is determined that the front end has reached the secondary transfer roller 19 (YES in step S304), in step S305, the surface property detection sensor control unit 370 measures the surface property of the recording material P by the surface property detection sensor. The amount of light received by the light receiving element 360 at this time is defined as a2. In step S306, the bending determination unit 2020 determines whether a value obtained by subtracting a2 from a1 is larger than a predetermined threshold. If the obtained value is larger than the predetermined threshold (YES in step S306), the bending determination unit 2020 determines that bending has occurred. When the bending does not occur (NO in step S306), then in step S307, the grammage detection sensor control unit 300 measures the grammage. Then in step S308, the type determination unit 2030 determines the type of recording material P based on the grammage. On the other hand, when the bending has occurred (YES in step S306), then in step S309, the type determination unit 2030 performs control for removing the bending of the recording material P by decreasing the rotation speed of the conveyance roller 63. In step S310, the image formation control unit 3 determines whether the rear end of the recording material P has passed through the conveyance roller 63, and if not (NO in step S301), the processing is repeated from step S305 until the rear end of the recording material P passes through the roller 63.

In the present exemplary embodiment, the rotation speed of the conveyance roller 63 is controlled in step S309 for removing the bending. Alternatively, the rotation speed of the secondary transfer roller 19 may be controlled. Occurrence of bending decreases the intensity (amplitude) of the ultrasonic wave received by the grammage detection sensor. Accordingly, occurrence of the bending may be determined based on the detection results obtained by the grammage detection sensor, instead of the surface property detection sensor, before and after the recording material P has reached the counter position of the secondary transfer roller 19. Furthermore, occurrence of bending decreases the amount of light received by the thickness detection sensor. Accordingly, occurrence of bending may be determined based on the detection results obtained by the thickness detection sensor, instead of the surface property detection sensor, before and after the recording material P has reached the counter position of the secondary transfer roller 19. Furthermore, in the present exemplary embodiment, the sensor used for determining occurrence of bending and the sensor used for determining the type of recording material are separately provided. However, the same sensor may be used for these purposes.

In this manner, in the present exemplary embodiment, occurrence of bending is detected by comparing the detection results obtained by the sensor before and after the recording material P has reached the counter position of the secondary transfer roller 19. When bending is detected, detection of the recording material type is not performed after the recording material P has reached the counter position of the secondary transfer roller 19. This configuration enables improvement in the detection accuracy of the recording material type. Furthermore, when bending is detected, it is possible to control a conveyance member of the recording material P to remove the bending.

The above-described exemplary embodiments have mainly described the case where the number of the target recording material P is one. When successively performing printing on a plurality of recording materials P, the succeeding recording materials P are likely to have the same type as the first recording material P. Thus, the type determination processing may not be performed on the succeeding recording materials P.

Alternatively, control may be performed such that the measurement of the succeeding (second and subsequent) recording materials P can be switched based on the measurement result of the first recording material P. That is, whether bending occurs is determined based on the type of recording material P that has been determined in a state in which the first recording material P has not reached the counter position of the secondary transfer roller 19. If it is determined that bending may occur in the first recording material P, type determination for the recording material P is stopped after the second and subsequent recording materials P following the first recording material P have reached the counter position of the secondary transfer roller 19. On the other hand, if it is determined that bending does not occur in the first recording material P, type determination for the recording material P is performed after the second and subsequent recording materials P following the first recording material P have reached the counter position of the secondary transfer roller 19.

The exemplary embodiments of the present invention can also be implemented by processing of supplying a program for implementing one or more functions of the above-described exemplary embodiments to a system or an apparatus via a network or a storage medium, and one or more processors in a computer of the system or the apparatus reading and executing the program. The exemplary embodiments of the present invention can also be implemented by a circuit (for example, application-specific integrated circuit (ASIC)) that implements one or more functions.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2014-233131, filed Nov. 17, 2014, and No. 2014-242303, filed Nov. 28, 2014, which are hereby incorporated by reference herein in their entirety.

What is claimed is:

1. An image forming apparatus configured to form an image on a recording material, the image forming apparatus comprising:
    an ultrasonic wave detection unit including a transmission element configured to transmit an ultrasonic wave and a reception element configured to receive the ultrasonic wave transmitted from the transmission element;
    a first conveyance roller arranged on an upstream side of the ultrasonic wave detection unit in a conveyance direction of the recording material, and configured to convey the recording material toward a position between the transmission element and the reception element;
    a second conveyance roller arranged on a downstream side of the ultrasonic wave detection unit in the conveyance direction, and configured to convey the recording material conveyed by the first conveyance roller,
    wherein the first conveyance roller and the second conveyance roller form a loop on the recording material by conveying the recording material at respective different speeds; and
    a processor configured to control an image forming condition for forming the image on the recording material, based on the ultrasonic wave received by the reception element via the recording material in a first period and not based on the ultrasonic wave received by the reception element via the recording material in a second period,
    wherein the first period is a period in which no loop is formed on the recording material, and the second period is a period in which a loop is formed on the recording material by the first conveyance roller and the second conveyance roller.

2. The image forming apparatus according to claim 1, wherein the first period is a period in which the recording material is conveyed by either one of the first conveyance roller and the second conveyance roller, and the recording material is not conveyed by the other one.

3. The image forming apparatus according to claim 2, wherein the first period is a period from a time point at which a front end of the recording material passes through the position between the transmission element and the reception element to a time point at which the front end of the recording material reaches the second conveyance roller.

4. The image forming apparatus according to claim 2, wherein the first period is a period from a time point at which a rear end of the recording material passes through the first conveyance roller to a time point at which the rear end of the recording material passes through the position between the transmission element and the reception element.

5. The image forming apparatus according to claim 1, wherein the second period is a period in which the recording material is conveyed by both of the first conveyance roller and the second conveyance roller.

6. The image forming apparatus according to claim 5, wherein the second period is a period from a time point at which a front end of the recording material reaches the second conveyance roller to a time point at which a rear end of the recording material passes through the first conveyance roller.

7. The image forming apparatus according to claim 1, wherein the transmission element and the reception element are arranged facing each other, and the reception element receives the ultrasonic wave transmitted through the recording material.

8. The image forming apparatus according to claim 1, wherein the processor controls the image forming condition based on the ultrasonic wave received by the reception element via the recording material in a period in which a conveyance speed of the recording material is constant.

9. The image forming apparatus according to claim 1, wherein the processor controls the image forming condition based on the ultrasonic wave received by the reception element via the recording material in a period in which a conveyance speed of the recording material is increased or decreased.

10. The image forming apparatus according to claim 1, further comprising a light detection unit including a light emitting element configured to emit light and a light receiving element configured to receive the emitted light emitted from the light emitting element,
    wherein the processor controls the image forming condition based on the light received by the light receiving element via the recording material.

11. The image forming apparatus according to claim 10, wherein the light receiving element receives the light reflected on the recording material.

12. The image forming apparatus according to claim 10, wherein the light receiving element is an image capturing sensor configured to capture received light as a surface image.

13. The image forming apparatus according to claim 10, wherein the processor controls the image forming condition based on the light received by the light receiving element via the recording material in a period in which a conveyance speed of the recording material is constant.

14. The image forming apparatus according to claim 10, wherein the processor controls the image forming condition not based on the light received by the light receiving element via the recording material in a period in which a conveyance speed of the recording material is increased or decreased.

15. The image forming apparatus according to claim 10, wherein the light emitting element does not emit the light onto the recording material in a period in which a conveyance speed of the recording material is increased or decreased.

16. The image forming apparatus according to claim 10, wherein the ultrasonic wave detection unit and the light detection unit are arranged in a direction orthogonal to the conveyance direction.

17. The image forming apparatus according to claim 10, further comprising a contact member configured to contact the recording material irradiated with light, on a second surface of the recording material that is opposite to a first surface irradiated with light,
    wherein the light emitting element emits the light onto a predetermined region of the first surface, and the contact member contacts the recording material in a predetermined region of the second surface that is opposite to the predetermined region of the first surface.

18. The image forming apparatus according to claim 1, wherein the second conveyance roller is a transfer roller configured to transfer an image onto the recording material conveyed by the first conveyance roller.

19. The image forming apparatus according to claim 1, further comprising a fixing unit configured to fix an image onto the recording material, and
    wherein the image forming condition is a fixing temperature at which the fixing unit fixes the image onto the recording material.

20. The image forming apparatus according to claim 1, further comprising a transfer roller configured to transfer an image onto the recording material,
    wherein the image forming condition is a transfer voltage to be applied to the transfer roller.

21. An image forming apparatus configured to form an image on a recording material, the image forming apparatus comprising:
    an ultrasonic wave detection unit including a transmission element configured to transmit an ultrasonic wave and a reception element configured to receive the ultrasonic wave transmitted from the transmission element;
    a first conveyance roller arranged on an upstream side of the ultrasonic wave detection unit in a conveyance direction of the recording material, and configured to convey the recording material toward a position between the transmission element and the reception element;
    a second conveyance roller arranged on a downstream side of the ultrasonic wave detection unit in the conveyance direction, and configured to convey the recording material conveyed by the first conveyance roller,
    wherein a conveyance speed of the recording material by the first conveyance roller is faster than a conveyance speed of the recording material by the second conveyance roller; and
    a processor configured to control an image forming condition for forming the image on the recording material, based on the ultrasonic wave received by the reception element via the recording material in a first period and not based on the ultrasonic wave received by the reception element via the recording material in a second period,
    wherein the first period is a period in which the recording material is conveyed by either one of the first conveyance roller and the second conveyance roller, and the recording material is not conveyed by the other one, and
    wherein the second period is a period in which the recording material is conveyed by both of the first conveyance roller and the second conveyance roller.

22. The image forming apparatus according to claim 21, further comprising a light detection unit including a light emitting element configured to emit light and a light receiving element configured to receive the light emitted from the light emitting element,
    wherein the processor controls the image forming condition based on the light received by the light receiving element via the recording material.

23. The image forming apparatus according to claim 22, wherein the processor controls the image forming condition based on the light received by the light receiving element via the recording material in a period in which a conveyance speed of the recording material is constant and not based on the light received by the light receiving element via the recording material in a period in which a conveyance speed of the recording material is increased or decreased.

24. The image forming apparatus according to claim 22, wherein the processor controls the image forming condition based on the light received by the light receiving element via the recording material in a period in which a conveyance speed of the recording material is constant, and wherein the light emitting element does not emit the light onto the recording material in a period in which a conveyance speed of the recording material is increased or decreased.

25. The image forming apparatus according to claim 23, further comprising a contact member configured to contact the recording material irradiated with light, on a second surface of the recording material that is opposite to a first surface irradiated with light,
wherein the light emitting element emits the light onto a predetermined region of the first surface, and the contact member contacts the recording material in a predetermined region of the second surface that is opposite to the predetermined region of the first surface.

26. The image forming apparatus according to claim 25, wherein the second conveyance roller is a transfer roller configured to transfer an image onto the recording material conveyed by the first conveyance roller.

27. The image forming apparatus according to claim 26, wherein the first period includes the period in which the conveyance speed of the recording material is increased or decreased, and the second period includes the period in which the conveyance speed of the recording material is constant.

28. An image forming apparatus configured to form an image on a recording material, the image forming apparatus comprising:
an ultrasonic wave detection unit including a transmission element configured to transmit an ultrasonic wave and a reception element configured to receive the ultrasonic wave transmitted from the transmission element;
a first conveyance roller arranged on an upstream side of the ultrasonic wave detection unit in a conveyance direction of the recording material, and configured to convey the recording material toward a position between the transmission element and the reception element;
a second conveyance roller arranged on a downstream side of the ultrasonic wave detection unit in the conveyance direction, and configured to convey the recording material conveyed by the first conveyance roller,
wherein the first conveyance roller and the second conveyance roller form a loop on the recording material by conveying the recording material at respective different speeds; and
a processor configured to control an image forming condition for forming the image on the recording material, based on the ultrasonic wave received by the reception element via the recording material in a first period, the first period being a period in which no loop is formed on the recording material,
wherein the transmission element does not transmit the ultrasonic wave to the recording material in a second period, the second period being a period in which a loop is formed on the recording material by the first conveyance roller and the second conveyance roller.

29. An image forming apparatus configured to form an image on a recording material, the image forming apparatus comprising:
an ultrasonic wave detection unit including a transmission element configured to transmit an ultrasonic wave and a reception element configured to receive the ultrasonic wave transmitted from the transmission element;
a first conveyance roller arranged on an upstream side of the ultrasonic wave detection unit in a conveyance direction of the recording material, and configured to convey the recording material toward a position between the transmission element and the reception element;
a second conveyance roller arranged on a downstream side of the ultrasonic wave detection unit in the conveyance direction, and configured to convey the recording material conveyed by the first conveyance roller,
wherein a conveyance speed of the recording material by the first conveyance roller is faster than a conveyance speed of the recording material by the second conveyance roller; and
a processor configured to control an image forming condition for forming the image on the recording material, based on the ultrasonic wave received by the reception element via the recording material in a first period, the first period being a period in which the recording material is conveyed by either one of the first conveyance roller and the second conveyance roller, and the recording material is not conveyed by the other one,
wherein the transmission element does not transmit the ultrasonic wave to the recording material in a second period, the second period being a period in which the recording material is conveyed by both of the first conveyance roller and the second conveyance roller.

30. The image forming apparatus according to claim 29, further comprising a light detection unit including a light emitting element configured to emit light and a light receiving element configured to receive the light emitted from the light emitting element,
wherein the processor controls the image forming condition based on the light received by the light receiving element via the recording material.

31. The image forming apparatus according to claim 30, wherein the processor controls the image forming condition based on the light received by the light receiving element via the recording material in a period in which a conveyance speed of the recording material is constant and not based on the light received by the light receiving element via the recording material in a period in which a conveyance speed of the recording material is increased or decreased.

32. The image forming apparatus according to claim 30, wherein the processor controls the image forming condition based on the light received by the light receiving element via the recording material in a period in which a conveyance speed of the recording material is constant, and wherein the light emitting element does not emit the light onto the recording material in a period in which a conveyance speed of the recording material is increased or decreased.

33. The image forming apparatus according to claim 32, further comprising a contact member configured to contact the recording material irradiated with light, on a second surface of the recording material that is opposite to a first surface irradiated with light,
wherein the light emitting element emits the light onto a predetermined region of the first surface, and the contact member contacts the recording material in a predetermined region of the second surface that is opposite to the predetermined region of the first surface.

34. The image forming apparatus according to claim 33, wherein the second conveyance roller is a transfer roller configured to transfer an image onto the recording material conveyed by the first conveyance roller.

35. The image forming apparatus according to claim 34, wherein the first period includes the period in which the conveyance speed of the recording material is increased or decreased, and the second period includes the period in which the conveyance speed of the recording material is constant.

* * * * *